United States Patent
Nirogi et al.

(10) Patent No.: US 8,318,725 B2
(45) Date of Patent: Nov. 27, 2012

(54) ARYL INDOLYL SULFONAMIDE COMPOUNDS AND THEIR USE AS 5-HT$_6$ LIGANDS

(75) Inventors: Ramakrishna Nirogi, Hyderabad (IN); Rama Sastri Kambhampati, Hyderabad (IN); Anil Karbhari Shinde, Hyderabad (IN); Ishtiyaque Ahmad, Hyderabad (IN); Nagaraj Vishwottam Kandikere, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 0 days.

(21) Appl. No.: 13/119,385

(22) PCT Filed: Mar. 3, 2009

(86) PCT No.: PCT/IN2009/000143
§ 371 (c)(1), (2), (4) Date: Apr. 8, 2011

(87) PCT Pub. No.: WO2010/032257
PCT Pub. Date: Mar. 25, 2010

(65) Prior Publication Data
US 2011/0281849 A1    Nov. 17, 2011

(30) Foreign Application Priority Data
Sep. 17, 2008  (IN) ............................ 2263/CHE/2008

(51) Int. Cl.
*A01N 43/62*     (2006.01)
*A61K 31/55*     (2006.01)

(52) U.S. Cl. .................. 514/218; 514/254.09; 540/575; 544/373

(58) Field of Classification Search ................. 514/218, 514/254.09; 540/575; 544/373
See application file for complete search history.

(56) References Cited

U.S. PATENT DOCUMENTS 7,276,516 B2 * 10/2007 Allen et al. .................. 514/300
7,595,339 B2 *  9/2009 Allen et al. .................. 514/418

FOREIGN PATENT DOCUMENTS

| WO | 9827081 A1 | 6/1998 |
|---|---|---|
| WO | 9902502 A2 | 1/1999 |
| WO | 9937623 A2 | 7/1999 |
| WO | 9942465 A2 | 8/1999 |
| WO | 0063203 A1 | 10/2000 |
| WO | 0132646 A2 | 5/2001 |
| WO | 0236562 A2 | 5/2002 |
| WO | 02060871 A2 | 8/2002 |
| WO | 02098857 A1 | 12/2002 |
| WO | 02098878 A1 | 12/2002 |
| WO | 03013510 A1 | 2/2003 |
| WO | 03065046 A2 | 8/2003 |
| WO | 03066056 A1 | 8/2003 |
| WO | 03080580 A2 | 10/2003 |
| WO | 2004035047 A1 | 4/2004 |
| WO | 2004048328 A2 | 6/2004 |
| WO | 2004048330 A1 | 6/2004 |
| WO | 2004048331 A1 | 6/2004 |
| WO | 2004055026 A1 | 7/2004 |
| WO | 2005013974 A1 | 2/2005 |
| WO | 2007020652 A1 | 2/2007 |
| WO | 2008084491 A1 | 8/2008 |
| WO | 2008084492 A1 | 8/2008 |
| WO | 2008101247 A2 | 8/2008 |

OTHER PUBLICATIONS

Demchyshyn, L.L., ALX-1161: Pharmacological Properties of a Potent and Selective 5-HT6 Receptor Antagonist, Neuroscience 2001 Abstract, 2001, Society for Neuroscience, online.
Bentley, Jane C. et al. Investigation of stretching behaviour induced by the selective 5-HT6 receptor antagonist, Ro 04-6790, in rats, British Journal of Pharmacology, 1999, pp. 1537-1542, vol. 126, Stockton Press.
Berge, Stephen M., Pharmaceutical Salts, Journal of Pharmaceutical Sciences, Jan. 1977, pp. 1-19, vol. 66, No. 1, Wiley Periodicals, Inc.
Bonhaus, D.W., RO4368554, a high affinity, selective, CNS penetrating 5-HT6 receptor antagonist, Neuroscience 2002 Abstract, 2002, Society for Neuroscience, online.
Branchek, Theresa A., 5-HT6 Receptors as Emerging Targets for Drug Discovery, Annu. Rev. Pharmacol. Toxicol., 2000, pp. 319-334, vol. 40, Annual Reviews.

(Continued)

*Primary Examiner* — Noble Jarrell
*Assistant Examiner* — Valerie Rodriguez-Garcia
(74) *Attorney, Agent, or Firm* — IpHorgan Ltd.

(57) ABSTRACT

The present invention relates to novel aryl indolyl sulfonamide compounds of the formula (I), their tautomeric forms, their stereoisomers, their polymorphs, their pharmaceutically acceptable salts, their pharmaceutically acceptable solvates described herein and pharmaceutically acceptable compositions containing them.

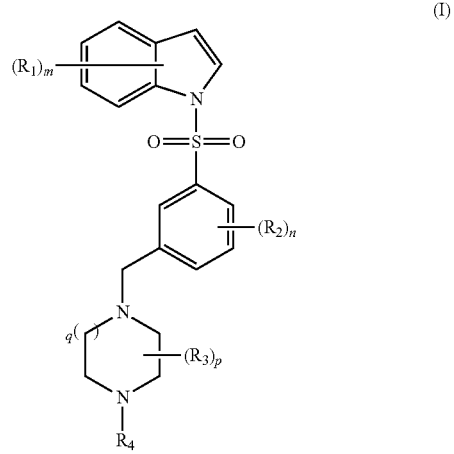

(I)

5 Claims, No Drawings

OTHER PUBLICATIONS

Bromidge, Steven M. et al., 5-Chloro-N-(4-methoxy-3-piperazin-1-ylphenyl)-3-methyl-2-benzothiophenesulfonamide (SB-271046): A Potent, Selective, and Orally Bioavailable 5-HT6 Receptor Antagonist, J. Med. Chem, 1999, pp. 202-205, vol. 42, ACS Publications.

Bromidge, Steven M. et al., Phenyl Benzenesulfonamides are Novel and Selective 5-HT6 Antagonists: Identi® cation of N-(2,5-Dibromo-3-uorophenyl)-4-methoxy-3-piperazin-1-ylbenzenesulfonamide (SB-357134), Bioorganic & Medicinal Chemistry Letters 11, 2001, pp. 55-59, Elsevier Ltd.

Reavill, C. et al., The therapeutic potential of 5-HT6 receptor antagonists, Current Opinion in Investigational Drugs, 2001, pp. 104-109, vol, 2, No. 1, PharmaPress Ltd.

Callahan, P.M., Characterization of the selective 5-HT6 receptor antagonist SB 271046 in behavioral models of cognition, Neuroscience 2004 Abstract, 2004, Society for Neuroscence, online.

Monsma, Frederick J., Cloning and Expression of a Novel Serotonin Receptor with High Affinity for Tricyclic Psychotropic Drugs, Molecular Pharmacology, 1993, pp. 320-327, vol. 43(3), Molecular Neuropharmacology Section, National Institute of Neurological Disorders and Stroke, National Institutes of Health, Bethesda, Maryland.

Dawson, L.A. et al., In vivo effects of the 5-HT6 antagonist SB-271046 on striatal and frontal cortex extracellular concentrations of noradrenaline, dopamine, 5-HT, glutamate and aspartate, British Journal of Pharmacology (2000), 2000, pp. 23-26, vol. 230 (1), Macmillan Publishers Ltd.

Ennaceur, A. et al., A new one-trial test for neurobiological studies of memory in rats. 1" Behavioral data, Behavioural Brain Research, 1998, pp. 47-59, vol. 31, Elsevier Ltd.

Ernst, Monique et al., DOPA Decarboxylase Activity in Attention Deficit Hyperactivity Disorder Adults. A [Fluorine-18] Fluorodopa Positron Emission Tomographic Study, The Journal of Neuroscience, Aug. 1, 1998, pp. 5901-5907, vol. 18 (15), Society for Neuroscience, National Institute of Health.

Fox, Gerard B. et al., Memory Consolidation Induces a Transient and Time-Dependent Increase in the Frequency of Neural Cell Adhesion Molecule Polysialylated Cells in the Adult Rat Hippocampus, Journal of Neurochemistry, 1995, pp. 2796-2799, vol. 65, No. 6, Lippencott-Raven Publishers.

Gerard, Caroline, Immuno-localization of serotonin 5-HT receptor-like material in the rat 6 central nervous system, Brain Research, 1997, pp. 207-219, vol. 746, Elsevier Science B.V.

Glennon, Richard A. et al., 2-Substituted Tryptamines: Agents with Selectivity for 5-HT6 Serotonin Receptors, Journal of Medicinal Chemistry, 2000, pp. 1011-1018, vol. 43, No. 5, ACS Publications.

Holenz, Jorg et al., Medicinal chemistry strategies to 5-HT6 receptor ligands as potential cognitive enhancers and antiobesity agents, Drug Discovery Today, Apr. 2006, pp. 283-299, vol. 11, No. 7/8, Elsevier.

Kask, Ants et al., Neuropeptide YY receptor antagonist CGP71683A: the effects on food 5 intake and anxiety-related behavior in the rat, European Journal of Pharmacology, 2001, pp. 215-224, vol. 414, Elsevier.

King. M. V. et al., 5-HT6 receptor antagonists reverse delay-dependent deficits in novel object discrimination by enhancing consolidation—an effect sensitive to NMDA receptor antagonism, Neuropharmacology, 2004, pp. 195-204, vol. 47, Elsevier Ltd.

Kohen, Ruth et al., Cloning, Characterization, and Chromosomal Localization of a Human 5-HT6 Serotonin Receptor, Journal of Neurochemistry, 1996, pp. 47-56, vol. 66, No. 1, Lippincott-Raven Publishers.

Linder, Mark D., An Assessment of the Effects of Serotonin 6 (5-HT6) Receptor Antagonists in Rodent Models of Learning, The Journal of Pharmacology and Experimental Therapeutics, 2003, pp. 682-691, vol. 307, The American Society for Pharmacology and Experimental Therapeutics.

Matteson, Cecilia et al., 2-Alkyl-3-(1,2,3,6-tetrahydropyridin-4-yl)-1H-indoles as novel 5-HT6 receptor agonists, Bioorganic & Medicinal Chemistry Letters 15, 2005, pp. 4230-4234, Elsivier Ltd.

Cole, Derek C. et al., MEDI 17—Discovery of a potent, selective and orally active 5-HT6 receptor agonist, 2005, abstract from Division of Medicinal Chemistry, The 230th ACS National Meeting.

Pouzet, B. et al., Effects of the 5-HT6 receptor antagonist, SB-271046, in animal models for schizophrenia, Pharmacology, Biochemistry and Behavior, 2002, pp. 635-643, vol. 71, Elsevier Science Inc.

Pullagurla, Manik R. et al., Possible differences in modes of agonist and antagonist binding at human 5-HT6 receptors, Bioorganic & Medicinal Chemistry Letters 14, 2004, pp. 4569-4573, Elsevier Ltd.

Rogers, D.C. et al., The Selective 5HT6 Receptor Antagonist, SB-271046-A, Enhances Performance of Maze Tasks in the Rat (abstract view), 2000, ScholarOne, Inc.

Roth, Bryan L. et al., Binding of Typical and Atypical Antipsychotic Agents to 5-Hydroxytryptamine-6 and 5-Hydroxytryptamine-7 Receptors, The Journal of Pharmacology and Experimental Therapeutics, 1994, pp. 1403-1410, vol. 268, Tb. American Socisty for Pharmacology and Experimental Therapeutics.

Routledge, Carol et al., Characterization of SB-271046: A potent, selective and orally active 5-HT6 receptor antagonist, British Journal of Pharmacology, 2000, pp. 1606-1612, vol. 130 (7), Macmillan Publishers Ltd.

Ruat, Martial et al., A novel rat serotonin (5-HT6) receptor: molecular cloning, localization and stimulation of camp accumulation, Biochemical and Biophysical Research Communications, May 28, 1993, pp. 268-276, vol. 193, No. 1, Academic Press, Inc.

Sleight, Andrew J., Characterization of Ro 04-6790 and Ro 63-0563: potent and selective antagonists at human and rat 5-HT6 receptors, British Journal of Pharmacology, 1998, pp. 556-562, vol. 124, Stockton Press.

Hirst, W. D. et al., Characterisation of SB-399885, a potent and selective 5-HT6 receptor antagonist, Neuroscience 2003 Abstract, Society for Neuroscience, 2003, online.

Stean, Tania et al., Anticonvulsant Properties of the Selective 5-HT6Receptor Antagonist SB-271046 in the Rat Maximal Electroshock Seizure Threshold Test, Br. J. of Pharmacol, 1999, p. 131P.

Tsai, Yuching et al., N1-(Benzenesulfonyl)tryptamines as Novel 5-HT6 Antagonists, Bioorganic & Medicinal Chemistry Letters 10, 2000, pp. 2295-2299, Elsevier Science Ltd.

Turnbull, Andrew V. et al., Selective Antagonism of the NPY Y5 Receptor Does Not Have a Major Effect on Feeding in Rats, Diabetes, Aug. 2002, pp. 2441, 2449, vol. 51, American Diabetes Association.

Ward, R. P. et al., Localization of Serotonin Subtype 6 Receptor Messenger RNA in the Rat Brain by In Situ Hybridization Histochemistry, Neuroscience, 1995, pp. 1105-111, vol. 64, Elsevier Science Ltd.

Woolley, M.L., A role for 5-ht6 receptors in retention of spatial learning in the Morris water maze, Neuropharmacology, 2001, pp. 210-219, vol. 41, Elsevier Science Ltd.

Yamada, N. et al., Improvement of scopolamine-induced memory impairment by Z-ajoene in the water maze in mice, Pharmacology, Biochemistry and Behavior 78, 2004, pp. 787-791, Elsevier Inc.

\* cited by examiner

ARYL INDOLYL SULFONAMIDE COMPOUNDS AND THEIR USE AS 5-HT$_6$ LIGANDS

CROSS-REFERENCE TO RELATED APPLICATIONS

This application claims priority to International Application No. PCT/IN2009/000143, filed on March 3, 2009, which in turn claims priority to Indian Patent Application No. 2263/CHE/2008, filed Sep. 17, 2008, the contents of which are both hereby incorporated by reference.

FIELD OF INVENTION

The present invention relates to novel aryl indolyl sulfonamide compounds of the formula (I), their tautomeric forms, their stereoisomers, their polymorphs, their pharmaceutically acceptable salts, their pharmaceutically acceptable solvates described herein and pharmaceutically acceptable compositions containing them.

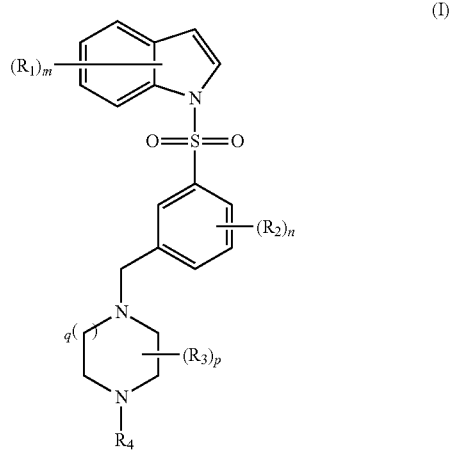

(I)

The present invention also relates to a process for the preparation of above said novel compounds, their tautomeric forms, their stereoisomers, their polymorphs, their pharmaceutically acceptable salts, their pharmaceutically acceptable solvates described herein and pharmaceutically acceptable compositions containing them. This invention also relates to the process of their preparation. This invention also relates to the novel intermediates involved therein and process of their preparation. These compounds are useful in the treatment/prevention of various disorders that are related to 5-HT$_6$ receptor functions:

BACKGROUND OF THE INVENTION

Various central nervous system disorders such as anxiety, depression, motor disorders etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity and neuroendocrine regulation among others. 5-HT receptor subtypes regulate the various effects of serotonin. Known 5-HT receptor family includes the 5-HT$_1$ family (e.g. 5-HT$_{1A}$), the 5-HT$_2$ family (e.g. 5-HT$_{2A}$ & 5-HT$_{2C}$), 5-HT$_3$, 5-HT$_4$, 5-HT$_5$, 5-HT$_6$ and 5-HT$_7$ subtypes.

The 5-HT$_6$ receptor subtype was first cloned from rat tissue in 1993 (Monsma, F. J.; Shen, Y.; Ward, R. P.; Hamblin, M. W., Sibley, D. R., Molecular Pharmacology, 1993, 43, 320-327) and subsequently from human tissue (Kohen, R.; Metcalf, M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J -M.; Tardivel-Lacombe, L.; Diaz, L.; Leurs, R.; Schwartz, J -C., Biochemical Biophysical Research Communications, 1993, 193, 268-276). The receptor is found almost exclusively in the central nervous system (CNS) areas both in rats as well as in humans.

In situ hybridization studies of 5-HT$_6$ receptor in rat brain using mRNA indicate principal localization in the areas of 5-1-IT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-HT$_6$ receptor mRNA has been observed in the olfactory tubercle, the striatum, nucleus accumbens and dentate gyms as well as CA$_1$, CA$_2$ and CA$_3$ regions of the hippocampus Lower levels of 5-HT$_6$ receptor, mRNA-mere seen in the granular layer of the cerebellum, several diencephalic nuclei, amygdala and in the cortex. Northern blots have revealed that 5-HT$_6$ receptor mRNA appears to be exclusively present in the brain, with little evidence for its presence in peripheral tissues.

Significant, efforts are being made to understand the possible role of the 5-HT$_6$ receptor in psychiatry, cognitive dysfunction, motor function and control, memory, mood and the like. The compounds which demonstrate a binding affinity for the 5-HT$_6$ receptor are earnestly sought both as an aid in the study of the 5-HT$_6$ receptor and as potential therapeutic agents in the treatment of central nervous system disorders, for example see Reavill C. and Rogers D. C., Current Opinion in Investigational Drugs, 2001, 2(1): 104-109, Pharma Press Ltd.

Monsma F. J. et al. (1993) and Kohen, R. et al. (2001) have shown that several tricyclic antidepressant compounds, such as amitriptyline and atypical antidepressant compounds, such as mianserin have high affinity for the 5-HT$_6$ receptor. These findings have led to the hypothesis that the 5-HT$_6$ receptor is, involved in the pathogenesis and/or treatment of affective disorders. Rodent models of anxiety-related behaviour yield conflicting results about the role of the 5-HT$_6$ receptor in anxiety. Treatment with 5-HT$_6$ receptor antagonists increases seizure threshold in a rat maximal electroconvulsive-shock test [Stean, T. et al. (1999) Anticonvulsant properties of the selective 5-HT$_6$ receptor antagonist SB-271046 in the rat maximal electroshock seizure threshold test. Br. J. Pharmacol. 127, 131P; Routledge, C. et al. (2000) Characterization of SB-271046: a potent, selective and orally active 5-HT$_6$ receptor antagonist. Br. J. Pharmacol. 130, 1606-1612]. Although this indicates that 5-HT$_6$ receptors might regulate seizure threshold, the effect is not as pronounced as that of known anticonvulsant drugs.

Our understanding of the roles of 5-HT$_6$ receptor ligands is most advanced in two therapeutic indications in which this receptor is likely to have a major role: learning and memory deficits and abnormal feeding behaviour. The exact role of the 5-HT$_6$ receptor is yet to be established in other CNS indications such as anxiety; although one 5-HT$_6$ agonist has reached Phase I clinical trials recently, the exact role of the receptor is still to be established and is the focus of significant investigation. There are many potential therapeutic uses for 5-HT$_6$ receptor ligands in humans based on direct effects and on indications from available scientific studies. These studies include the localization of the receptor, the affinity of ligands with known in-vivo activity and various animal studies conducted so far. Preferably, antagonist compounds of 5-HT$_6$ receptors are sought after as therapeutic agents.

One potential therapeutic use of modulators of 5-HT$_6$ receptor functions is in the enhancement of cognition and memory in human diseases such as Alzheimer's. The high levels of receptor found in structures such as the forebrain, including the caudate/putamen, hippocampus, nucleus accumbens and cortex suggests a role for the receptor in memory and cognition since these areas are known to play a vital role in memory (Gerard, C.; Martres, M. P.; Lefevre, K.; Miguel, M. C.; Verge, D.; Lanfumey, R.; Doucet, E.; Hamon, M.; E I Mestikawy, S., Brain Research, 1997, 746, 207-219). The ability of known 5-HT$_6$ receptor ligands to enhance cholinergic transmission also supports the potential cognition use (Bentley, J. C.;

Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine or 5-HT. This selective elevation of certain neurochemicals is noted during memory and cognition, strongly suggests a role for 5-HT$_6$ ligands in cognition (Dawson, L. A.; Nguyen, H. Q.; Li, P. British. Journal of Pharmacology, 2000, 130 (1), 23-26). Animal studies of memory and learning with a known selective 5-HT$_6$ antagonist has some positive effects (Rogers, D. C.; Hatcher, P. D.; Hagan, J. J. Society of Neuroscience, Abstracts, 2000, 26, 680).

A related potential therapeutic use for 5-HT$_6$ ligands is in the treatment of attention deficit disorders (ADD, also known as Attention Deficit Hyperactivity Disorder or ADHD) in children as well as adults. As 5-HT$_6$ antagonists appear to enhance the activity of the nigrostriatal dopamine pathway and ADHD has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

At present, a few fully selective agonists are available. The Wyeth agonist WAY-181187 is currently in Phase I trials to target anxiety [Cole, D. C. et al. (2005) Discovery of a potent, selective and orally active 5-HT$_6$ receptor agonist, WAY-181187. 230th ACS Natl. Meet. (August 28-September 1, Washington D.C.), Abstract MEDI 17.]

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$receptor and proposes that 5-HT$_6$ receptor is associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in-vivo studies in rats indicate that 5-HT$_6$ modulators may be useful in the treatment of movement disorders including epilepsy (Stean, T.; Routledge; C.; Upton, N., British Journal of Pharmacology, 1999, 127 Proc. Supplement-131 P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M.; British Journal of Pharmacology, 2000, 30 (7), 1606-1612).

Taken together, the above studies strongly suggest that compounds which are 5-HT$_6$ receptor modulators, i.e. ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive, disorders; the treatment of motion or motor disorders such as Parkinson's disease and epilepsy; the treatment of diseases associated with neurodegeneration such as stroke or head trauma; or withdrawal from drug addiction including addiction to nicotine, alcohol and other substances of abuse.

Such compounds are also expected to be of use in the treatment of certain gastrointestinal (GI) disorders such as functional bowel disorder. See for example, Roth, B. L.; et al., Journal of Pharmacology and Experimental Therapeutics, 1994, 268, pages 1403-1412; Sibley, D. R.; et al., Molecular Pharmacology, 1993, 43, 320-327.

Furthermore, the effect of 5-HT$_6$ antagonist and 5-HT$_6$ antisense oligonucleotides to reduce food intake in rats has been reported, thus potentially in treatment of obesity. See for example, Bentley, J. C.; Boursson, A.; Boess, F. G.; Kone, F. C.; Marsden, C. A.; Petit, N.; Sleight, A. J., British Journal of Pharmacology, 1999, 126 (7), 1537-1542); Wooley et al., Neuropharmacology, 2001, 41: 210-129, British Journal of Pharmacology (2006) 1-11, Petrus Johan Pauwels et al and WO 02/098878.

Recently a review by Holenz, Jo"rg et.al., Drug Discovery Today, 11, 7/8, April 2006, Medicinal chemistry strategies to 5-HT$_6$ receptor ligands as potential cognitive enhancers and antiobesity agents, gives elaborate discussion on evolution of 5-HT$_6$ ligands. It had summarized pharmacological tools and preclinical candidates used in evaluation of 5-HT$_6$ receptor in illnesses such as schizophrenia, other dopamine-related disorders and depression and to profile the neurochemical and electrophysiological effects of either blockade or activation of 5-HT$_6$ receptors. Furthermore, they have been used to characterize the 5-HT$_6$ receptor and to investigate its distribution.

So far several clinical candidates form the part of indole-type structures and are closely related structurallyto the endogenous ligand 541T, for example compounds by Glennon, RIA. et.al., 2-Substituted tryptamines: agents with selectivity for 5-HT$_6$ serotonin receptors, J. Med.

Chem. 43, 1011-1018, 2000; Tsai, Y. et.al., N1-(Benzenesulfonyl)tryptamines as novel 5-HT$_6$ antagonists, Bioorg. Med. Chem. Lett. 10, 2295-2299; 2000; Demchyshyn L. et al., ALX-1161: pharmacological properties of a potent and selective 5-FIT$_6$ receptor antagonist, 31st Annu. Meet. Soc. Neurosci. (Nov 10-15), Abstract 266.6, 2001; Slassi, A. et.al., Preparation of 1-(arylsulfonyl)-3-(tetrahydiopyridinypindoles as 54IT$_6$ receptor inhibitors, WO 200063203, 2000; Mattsson, C. et.al., Novel, potent and selective 2-alkyl-3-(1, 2,3,6-tetrahydropyridin-4-yl)-1H-indole as 5-HT$_6$ receptor agonists, XVIIth International Symposium on Medicinal Chemistry, 2002; Mattsson, C. et.al., 2-Alkyl-341,2,3,6-tetrahydropyridin-4-yl)-1H-indoles as novel 5-HT$_6$ receptor agonists, Bioorg. Med. Chem. Lett. 15, 4230-4234, 2005]

Structure functionality relationships are described in the section on indole-like structures and in a receptor-modeling study in which Pullagurla et al., claim different binding sites for agonists. and antagonists [Pullagurla, M. R. et al. (2004) possible differences in modes of agonist and antagonist binding at human 5-HT$_6$ receptors. Bioorganic Medicinal Chemistry Letters, 14, 4569-4573]. Most antagonists that are reported form part of the monocyclic, bicyclic and tricyclic. aryl-piperazine classes [Bromidge, S. M. et.al., (1999) 5-Chloro-N-(4-methoxy-3-piperazin-1-ylphenyl)-3-methyl-2-benzothiophenesulfonamide (SB-271046): A potent, selective and orally bioavailable 5-HT$_6$ receptor antagonist. J. Med. Chem. 42, 202-205; Bromidge, S. M. et al. (2001). Characterization of SB-399885, a potent and selective 5-HT$_6$ receptor antagonist. 33$^{rd}$ Annul Meet Society Neuroscience. (November 8-12, New Orleans), Abstract 576.7; Stadler, H. et al. (1999) 5-HT$_6$ antagonists: A novel approach for the symptomatic treatment of Alzheimer's disease. 37$^{th}$ IUPAC Cong. Berlin, Abstract MM-7; Bonhaus, D. W. et al. (2002) Ro-4368554, a high affinity, selective, CNS penetrating 5-HT$_6$ receptor antagonist. 32$^{nd}$ Annu. Meet. Soc. Neurosci., Abstract 884.5.; Beard, C. C. et al. (2002) Preparation of new indole derivatives with 5-HT$_6$ receptor affinity. WO patent 2002098857].

Ro 63-0563: Potent and selective antagonists at human and rat 5-HT$_6$ receptors. Br. J. Pharmacol. 124, (556-562). Phase II antagonist candidate from GlaxoSmithKline, SB-742457 for the therapeutic indication of cognitive dysfunction associated with Alzheimer's disease [Ahmed, M. et al. (2003) Novel compounds. WO patent 2003080580], and the Lilly compound LY-483518 [Filla, S. A. et al. (2002) Preparation of benzenesulfonic acid indol-5-yl esters as antagonists of the 5-HT$_6$ receptor, WO 2002060871]. SB-271046, the first 5-HT$_6$ receptor antagonist to enter Phase I clinical development, has been discontinued (probably because of low penetration of the blood-brain barrier). In addition, the selective 5-HT$_6$ receptor antagonist SB-271046 is inactive in animal tests related to either positive or negative symptoms of schizophrenia [Pouzet, B. et al. (2002) Effects of the 5-HT$_6$ receptor antagonist, SB-271046, in animal models for schizophrenia. Pharmacol. Biochem. Behav. 71, 635-643].

International Patent Publications WO 2007/046112, WO 2007/020653, WO2007/138611, WO 2005/066157, WO 2004/108671, WO 2004/048331, WO 2004/048330 and WO 2004/048328 (all assigned to Suven Life Sciences Limited) describe the related prior art. Further WO 98/27081, WO 99/02502, WO 99/37623, WO 99/42465 and WO 01/32646 (all assigned to Glaxo SmithKline Beecham PLC) disclose a series of aryl sulfonamide and sulfoxide compounds as 5-HT$_6$ receptor antagonists and are claimed to be useful in the treatment of various CNS disorders. While some 5-HT$_6$ modulators have been disclosed, there continues to be a need for compounds that are useful for modulating 5-HT$_6$. Surprisingly, it has been found that aryl indolyl sulfonamide compounds of formula (I) demonstrate very high 5-HT$_6$ receptor affinity. Therefore, it is an object of this invention to provide compounds, which are useful as therapeutic agents in the treatment of a variety of central nervous system disorders or disorders affected by the 5-HT$_6$ receptor.

SUMMARY OF THE INVENTION

The present invention relates to novel aryl indolyl sulfonamide compounds of the formula (I), their tautomeric forms, their stereoisomers, their polymorphs, their pharmaceutically acceptable salts, their pharmaceutically acceptable solvates described herein and pharmaceutically acceptable compositions containing them.

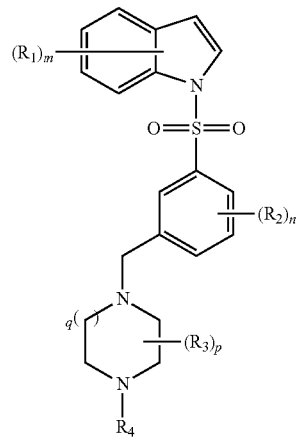

wherein $R_1$ $R_2$ and $R_3$ may be same or different and each independently represent hydrogen, halogen, $(C_1$-$C_3)$alkyl, $(C_1$-$C_3)$alkoxy, cyclo$(C_3$-$C_6)$alkyl, cyclo$(C_3$-$C_6)$alkoxy, halo $(C_1$-$C_3)$alkyl or halo $(C_1,C_3)$alkoxy;

$R_4$ represents hydrogen, $(C_1$-$C_3)$alkyl, cyclo$(C_3$-$C_6)$alkyl, halo$(C_1$-$C_3)$alkyl, aryl or aralkyl;

"m" represents 0 to 6;
"n" represents 0 to 4;
"p" represents 0 to 5;
"q" represents 0 to 2;

The present invention relates to use of a therapeutically effective amount of compound of formula (I), to manufacture a medicament in the treatment/prevention of various disorders that are related to 5-HT$_6$receptor functions.

Specifically, the compounds of this invention are useful in the treatment of various disorders such as anxiety, alzheimer's disease, depression, convulsive disorders, obsessive-compulsive disorders, migraine, headache, cognitive memory disorders, ADHD (Attention Deficient Disorder/Hyperactivity Syndrome), personality disorders, psychosis, paraphrenia, psychotic depression, parkinson's disease, mania, schizophrenia, panic disorders, sleep disorders, withdrawal from drug abuse syndrome, stroke, head trauma, mild cognitive impairment, neurodegenerative disorders, gastrointestinal and obesity.

In another aspect, the invention relates to pharmaceutical compositions containing a therapeutically effective amount of at least one compound of formula (I) or individual stereoisomers, racemic or non-racemic mixture of stereoisomers or pharmaceutically acceptable salts or solvates thereof, in admixture with at least one suitable carrier, diluents, adjuvants or excipients.

In another aspect, the invention also provides a radiolabeled compound of formula (I) for use in medical diagnosis or therapy, as well as the use of a radiolabeled compound of formula (I) to prepare a medicament useful in the treatment of various disorders that are related to 5-HT$_6$ receptor functions. In another aspect, the invention relates to compositions comprising and methods for using compounds of formula (I).

In still another aspect, the invention relates to the use of a compound according to the present invention in combination with at least one further active ingredient for manufacture of a medicament for the treatment or prevention of diseases and conditions.

In still another aspect, the invention relates to novel intermediate compounds and process of their preparation of general formula (II) and (III), which are useful in the preparation of compounds of general formula (I).

In yet another aspect, the invention further relates to the process for preparing compounds of formula (I).

Following is the Partial List of the Compounds Belonging to General Formula (I):

1-[4-Bromo-3-(4-ethyl piperazin-1-yl methyl) benzenesulfonyl]-1H-1-indole;
1-[4-Bromo-3-(4-methyl piperazin-1-yl methyl) benzenesulfonyl]-5-methoxy-1H-indole;
1-[4-Bromo-3-(4-ethyl piperazin-1-yl methyl) benzenesulfonyl]-5-methoxy-1H-indole;
1-[4-Bromo-3-(4-ethyl piperazin-1-yl methyl) benzenesulfonyl]-5-fluoro-1H-indole;
1-[4-Chloro-3-(4-methyl piperazin-1-yl methyl) benzenesulfonyl]-5-fluoro-3-bromo-1H-indole;
5-Isopropoxy-1-[3-(4-methyl piperazin-1-yl methyl) benzenesulfonyl]-1H-indole;
4-Chloro-1-[3-(4-methyl piperazin-1-yl methyl) benzenesulfonyl]-1H-indole;
1-[3-(4-Methyl piperazin-1-yl methyl) benzenesulfonyl]-1H-indole;
5-Methoxy-1-[3(4-methylpiperazin-1-yl methyl) benzenesulfonyl]-1H-1-indole;
5-Fluoro-1-[3-(4-methyl piperazin-1-yl methyl) benzenesulfonyl]-1H-indole;
5-Ethoxy=1-[3-(4-methyrpiperazin-1-yl methyl) benzenesulfonyl]-1H-indole;
1-[4-Bromo-3-(4-ethyl piperazin-1-yl methyl) beniene-sulfonyl]-1H-indole dihydrochloride;
1-[4-Chloro-3-(4-methyl piperazin-1-yl methyl) benzenesulfonyl]-1H-indole dihydrochloride;
1-[4-Chloro-3-(4-methyl piperazin-1-yl methyl) benzenesulfonyl]-5-fluoro-1H-indole dihydrochloride;
1-[4-Chloro-3-(4-ethyl piperazin-1-yl methyl) benzenesulfonyl]-1H-indole dihydrochloride;
1-[4-Chloro-3-(4-methyl piperazin-1-yl methyl) benzenesulfonyl]-5-methoxy-1H-indole dihydrochloride;
1-[4-Chloro-3-(4-methyl piperazin-1-yl methyl) benzenesulfonyl]-5-bromo-1H-indole dihydrochloride;
1-[4-Chloro-3-(4-ethyl piperazin-1-yl methyl) benzenesulfonyl]-5-methoxy-1H-1-indole dihydrochloride;
1-[4-Chloro-3-(4-ethyl piperazin-1-yl methyl) benzenesulfonyl]-4-chloro-1H-indole dihydrochloride;
1-[4-Chloro-3-(4-methyl piperazin-1-yl methyl) benzenesulfonyl]-4-chloro-1H-indole dihydrochloride;
1-[4-Bromo-3-(4-methyl piperazin-1-yl methyl) benzenesulfonyl]-1H-indole dihydrochloride;
1-[4-methyl-3-(4-methyl piperazin-1-yl methyl) benzenesulfonyl]-1H-indole dihydrochloride;
1-[4-methyl-3-(4-ethyl piperazin-1-yl methyl) benzenesulfonyl]-1H-indole dihydrochloride;
1-[4-methyl-3-(4-methyl piperazin-1-yl methyl) benzenesulfonyl]-5-methoxy-1H-indole dihydrochloride;
1-[4-Chloro-3-(4-ethyl piperazin-1-yl methyl) benzenesulfonyl]-5-fluoro-1H-indole dihydrochloride;
1-[4-Bromo-3-(4-methyl piperazin-1-yl methyl) benzenesulfonyl]-5-fluoro-1H-indole dihydrochloride;
1-[4-Bromo-3-(4-m ethyl piperazin-1-yl methyl) benzenesulfonyl]-5-methoxy-3-methyl-1H-indole dihydrochloride;
1-[4-Bromo-3-(4-methyl piperazin-1-yl methyl) benzenesulfonyl]-5-methoxy-3-methyl-1H-indole dihydrochloride;
1-[4-Chloro-3-(4-ethyl piperazin-1-yl methyl) benzenesulfonyl]-5-bromo-1H-indole dihydrochloride;
1-[4-Chloro-3-(4-ethyl piperazin-1-yl methyl) benzenesulfonyl]-5-methoxy-3-methyl-1H-indole dihydrochloride;
1-[4-Chloro-3-(4-methyl piperazin-1-yl methyl) benzenesulfonyl]-5-methoxy-3-methyl-1H-indole dihydrochloride;
1-[4-Chloro-3-(4-methyl piperazin-1-yl methyl) benzenesulfonyl]-5-methoxy-3-bromo-1H-indole dihydrochloride;
1-[4-Chloro-3-(4-ethyl piperazin-1-yl methyl) benzenesulfonyl]-5-methoxy-3-bromo-1H-indole dihydrochloride;
1-[4-Chloro-3-(4-ethyl piperazin-1-yl methyl) benzenesulfonyl]-3-methyl-1H-indole dihydrochloride;
1-[4-Chloro-3-(4-methyl piperazin-1-yl methyl) benzenesulfonyl]-3-methyl-1H-indole dihydrochloride;
1-[4-Bromo-3-(4-methyl piperazin-1-yl methyl) benzenesulfonyl]-5-bromo-1H-indole dihydrochloride;
1-[4-Bromo-3-(4-ethyl piperazin-1-yl methyl) benzenesulfonyl]-5-bromo-1H-indole dihydrochloride;
1-[4-Bromo-3-(4-methyl piperazin-1-ylmethyl) benzenesulfonyl]-3-methyl-1H-indole dihydrochloride;
1-[4-Bromo-3-(4-ethyl piperazin-1-yl methyl) benzenesulfonyl]-3-methyl-1H-indole dihydrochloride;
1-[4-Methyl-3-(4-ethyl piperazin-1-yl methyl) benzenesulfonyl]-5-methoxy-3-methyl-1H-indole dihydrochloride;
1-[4-Methyl-3-(4-methyl piperazin-1-yl methyl) benzenesulfonyl]-5-methoxy-3-methyl-1 H-indole dihydrochloride;
1-[4-Methyl-3-(4-ethyl piperazin-1-yl methyl) benzenesulfonyl]-5-methoxy-1H-indole dihydrochloride;
1-[4-Methyl-3-(4-methyl piperazin-1-yl methyl) benzenesulfonyl]-5-fluoro-1H-indole dihydrochloride;
1-[4-Methyl-3-(4-ethyl piperazin-1-yl methyl) benzenesulfonyl]-5-fluoro-1H-indole dihydrochloride;
1-[4-Chloro-3-(4-ethyl-[1,4]cliazepan-1-yl methyl) benzenesulfonyl]-3-methyl-1H-indole dihydrochloride;
1-[4-Chloro-3-(4-methyl[1,4]diazepan-1-yl methyl) benzenesulfonyl]-3-methyl-1H-indole dihydrochloride;
2-Bromo-1-[3-(4-methyl piperazin-1-yl methyl) benzenesulfonyl]-1H-indole;
4-Bromo-1-[3-(4-ethyl piperazin-1-yl methyl) benzenesulfonyl]-2-methyl-1H-indole;
7-Chloro-1-[3-(4-methyl piperazin-1-yl methyl) benzenesulfonyl]-2-methyl-1H-indole;
1-[2-Chloro-5-(4-methyl piperazin-1-yl methyl) benzenesulfonyl]-3-methyl -1H-indole and
1-[2-Bromo-5-(4-methyl-[1,4]-diazepan-1-yl methyl) benzenesulfonyl]-5-chloro-3-methyl-1H-indole; and its tautomeric forms, its stereoisomers, its polymorphs, its pharmaceutically acceptable salts'and solvates.

DETAILED DESCRIPTION OF THE INVENTION

Unless otherwise stated, the following terms used in the specification and claims have the meanings given below:

"Halogen" means fluorine, chlorine, bromine or iodine;

"$(C_1$-$C_3)$alkyl" means straight or branched chain alkyl radicals containing one to three carbon atoms and includes methyl, ethyl, n-propyl or iso-propyl;

"$(C_1$-$C_3)$alkoxy" means straight or branched chain alkyl radicals containing one to three carbon atoms and includes methoxy, ethoxy, propyloxy or iso-propyloxy;

"Cyclo$(C_3$-$C_6)$alkyl" means cyclic or branched cyclic alkyl radicals containing three to six carbon atoms and includes cyclopropyl, cyclobutyl, cyclopentyl, cyclopropylmethyl, cyclo$(C_3$-$C_6)$alkyl methyl or cyclohexyl, which may be substituted or unsubstituted and optionally the substituents may be selected from halogen, $(C_1$-$C_3)$alkyl or $(C_1$-$C_3)$ alkoxy; "Cyclo$(C_3$-$C_6)$alkoxy" means cyclic and branched cyclic alkyl radicals containing from three to six carbon atoms and includes cyclopropyloxy, cyclobutyloxy, cyclopentyloxy or cyclohexyloxy;

"Halo($C_1$-$C_3$)alkyl" means straight or branched chain alkyl radicals containing one to three carbon atoms and includes fluoromethyl, difluoromethyl, trifluoromethyl, trifluoroethyl, fluoroethyl, difluoroethyl and the like;

"Halo($C_1$-$C_3$)alkoxy" means straight or branched chain alkyl radicals containing one to three carbon atoms and includes fluoromethoxy, difluoromethoxy, trifluoromethoxy, trifluoroethoxy, fluoroethoxy, difluoroethoxy and the like;

"Aryl" means monocyclic-aromatic ring system; which can optionally be substituted with hydrogen, halogen, ($C_1$-$C_3$)alkyl, halo($C_1$-$C_3$)alkyl, ($C_1$-$C_3$)alkoxy or halo ($C_1$-$C_3$)alkoxy;

"Aralkyl" means benzyl or heterocyclylmethyl and the like;

The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition; American Psychiatric Association, Washington, D.C.

The phrase "pharmaceutically acceptable salts" indicates that the substance or composition must be compatible chemically and/or toxicologically, with the other ingredients comprising a formulation, the mammal being treated therewith.

"Therapeutically effective amount" is defined as 'an amount of a compound of the present invention that (i) treats or prevents the particular disease, condition or disorder (ii) attenuates, ameliorates or eliminates one or more, symptoms of the, particular disease, condition or disorder (iii) prevents or delays the onset of one or more symptoms of the particular disease, condition or disorder described herein'.

The terms "treating", "treat" or "treatment" embrace all the meanings such as preventative, prophylactic and palliative.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

Certain compounds of formula (I) are capable of existing in stereoisomeric forms (e. g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically, active isomers in a manner known per se. In the case of the compounds of general formula (I) having an asymmetric carbon atom the present invention relates to the D-form, the L-form and D,L— mixtures and in the case of a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other. by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming diastereomeric salts with chiral acids or chiral amines or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid and organic acids e. g. succinic, maleic, acetic, fumaric, citric, tartaric, benzoic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, tetrahydrofuran, methanol, ethanol, t-butanol, dioxane, isopropanol; isopropyl ether or mixtures thereof may be used.

The compounds of formula (I) may be prepared in crystalline or non-crystalline form and if crystalline, may optionally be solvated, eg. as the hydrate. This invention includes within its scope stoichiometric solvates (eg. hydrates) as well as compounds containing variable amounts of solvent (eg. water).

The compounds of the invention cam be used in combination, with each other or with other therapeutic agents or approaches used to treat or prevent the conditions listed above. Such agents or approaches include beta-secretase inhibitors; gamma-secretase inhibitors; amyloid aggregation inhibitors (e.g. Alzhemed); directly or indirectly acting neuroprotective compounds; anti-oxidants such as Vitamin E and ginkolides; anti inflammatory agents such as Cox-inhibitors or NSAID's; HMG-CoA Reductase Inhibitors (statins); acetyicholine-esterase inhibitors such as donepezil, rivastigmine, tacnne, galantamine; NMDA receptor antagonists (e.g. memantine); AMPA, agonists; compounds which modulate the release or concentration of neurotransmitters (e.g. NS-2330); compounds inducing the release of growth hormones (e.g. ibutamoren mesylate and capromorelin); CBI receptor antagonists or inverse agonists; antibiotika like minocyclin or rifampicin; PDE-IV and PDE-IX inhibitors; GABAA inverse agonists; nicotinic agonists: histamin H3 antagonists, 5-HT$_4$ agonists or partial agonists; 5-HT$_6$ antagonists; a2-adrenoreceptor antagonists; muscarinic M1 agonists; muscarinic M2 antagonists; metabotrophic glutamaic-receptor 5 positive modulators; and compounds, which modulate receptors oder enzymes in such a way, that the efficacy and/or safety of the compounds of the present invention is increased or side effects are reduced.

Preferred are such combinations comprising one or more of the compounds of the present invention and one or more additional active ingredient selected from the group consisting Alzhemed, vitamin E, ginkolide, donepezil, rivastigmine, tacnne, galantamine, memantine, NS-2330, ibutamoren mesylate, capromoreline, minocycline and rifampicine.

In the combination of the present invention, the compounds of the present invention and the above mentioned combination partners may be administered separately (e.g. kit of parts) or together in one pharmaceutical composition (e.g. capsule or tablet). In addition, the administration of one element of the combination of the present invention may be prior to, concurrent to, or subsequent to the administration of the other element of the combination of the present invention may be prior to, concurrent to, or subsequent to the administration of the other element of the combination. If the compounds of the present invention and the one or more additional active ingredient are present in separate formulations these separate formulations may be administered simultaneously or sequentially.

For the treatment or prevention of the above mentioned diseases and conditions compounds of the invention can be used in combination with immunological approaches, such as, for example, immunization with A beta peptide or derivatives thereof or administration of anti-A beta peptide antibodies.

Therefore, the invention relates to the use of a compound according to the present invention in combination with at least one further active ingredient for the manufacture of a medicament for the treatment or prevention of diseases and conditions.

Numerous radioisotopes are readily available including isotopes of hydrogen, carbon, nitrogen, oxygen, phosphorus, sulfur, iodine, fluorine, bromine & chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{123}$I, $^{124}$I, $^{125}$I, $^{131}$I, $^{18}$F, $^{25}$Br, $^{76}$Br, $^{77}$Br, $^{82}$Br & $^{36}$Cl.

A compound of formula (I) can be radiolabeled by using standard techniques known in organic chemistry. Alternatively, compound of formula (I) radiolabeled with radioisotope as a substituent in one of the starting materials or in an intermediate used in the synthesis of the compound of formula (I). For example, see Arthur Murry III, D. Lloyd Williams; Organic Synthesis with Isotopes, vol. I and II, Interscience Publishers Inc., N.Y. (1958) and Melvin Calvin et al. Isotopic Carbon John Wiley and Sons Inc., N.Y.(1949).

Synthesis of radiolabeled compounds may be conveniently performed by a radioisotope supplier specializing in custom synthesis of radiolabeled probe compounds, such as Amersham Corporation, Arlington Heights, IL; Cambrige Isotopes Laboratories, Inc. Andover, Mass.; Wizard Laboratories, West Sacramento, Calif.; ChemSyn Laboratories, Lexena, Kans.; American Radiolabeled Chemicals, Inc.& St. Louis, Mo.;

Radioalabeled analogues of compound of formula (I) may be used in clinical studies to evaluate the role of 5-HT$_6$ receptor ligands in a variety of diseases areas, where 5-HT$_6$ receptor ligands are believed to be involved.

Radiolabeled compounds of formula (I) are useful as imaging agents and biomarker for medical therapy and diagnosis. Such radiolabeled compounds are also useful as pharmacological tools for studying 5-HT$_6$ function and activity. For example, isotopically labeled compounds are particularly useful in SPECT (single photon emission compound tomography) and in PET (positron emission tomography).

The present invention also provides a process for the preparation (Scheme—I) of a compound of formula (I) or a pharmaceutically acceptable salt thereof, which comprises of the following route, wherein the novel intermediate compound of formula (III) is synthesized as described in preparation 3.

Scheme - I

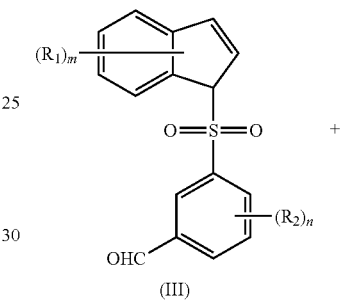

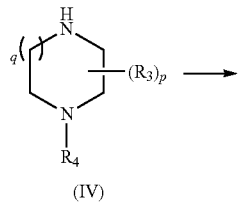

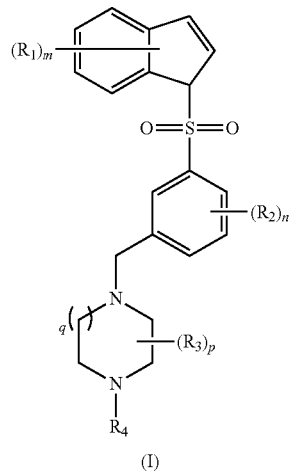

The process of this invention includes, contacting a compound of the following formula (III),

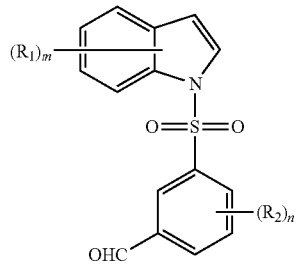
(III)

with compound of formula (IV) by reductive amination,

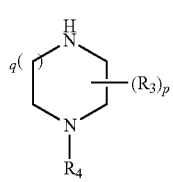
(IV)

by using a suitable reducing agent in presence of inert solvent at ambient temperature to obtain a compound of formula (I), wherein all substitutions are described as earlier.

The above reaction is carried out in a solvent such as tetrahydrofuran, toluene, dimethylformamide, dimethyl sulfoxide, dimethyl ether, ethylene dichloride, chloroform and the like or a mixture thereof and preferably using ethylene dichloride and chloroform. The reaction is carried by using reducing agents like sodium borohydride, sodium triacetoxy borohydride, sodium cyanoborohydride and the like or a mixture thereof and preferably using sodium triacetoxy borohydride. The reaction temperature may range from 20° C. to 50° C. based on the choice of solvent and preferably at a temperature in the range from 25° C. to 35° C. The duration of the reaction may range from 3 to 8 hours, preferably from a period of 4 to 7 hours.

The compound of formula (I) is converted into salts by convenient derivatization. By using methanolic hydrochloric acid in suitable solvent, the above reaction can be carried out. The inert atmosphere may be maintained by using inert gases such as $N_2$, Ar or He. The reaction-temperature may range from 20° C. to 40° C. and preferably at a temperature in the range from 25° C. to 35° C. The duration of the reaction may range from 0.5 to 4 hours, preferably from a period of 1 to 3 hours.

According to a feature of the present invention, the novel intermediate compound of general formula (III) is prepared by using novel intermediate compound of general formula (II).

Novel intermediate compound of general formula (II) are represented as given below, wherein all symbols are as defined earlier:

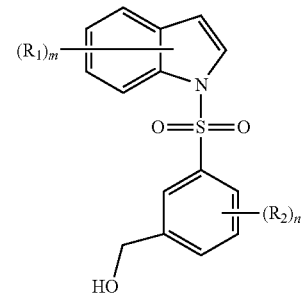
(II)

The present invention also provides a process for the preparation of a novel intermediate compound of general formula (II), which comprises of the following route, wherein the compound of formula (A) is synthesized as described in preparation 1.

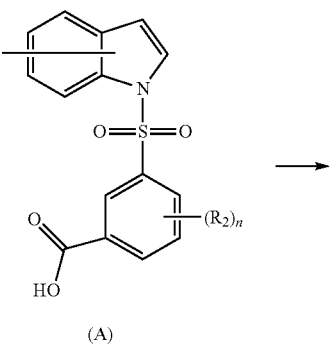
(A)

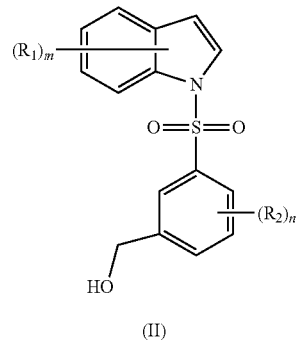
(II)

The process of this invention includes, reduction of compound of formula (A),

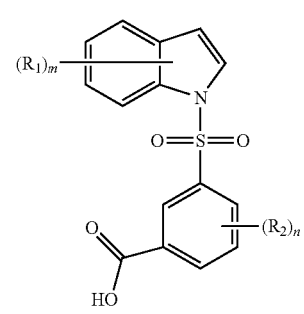
(A)

by using a suitable reducing agent in presence of suitable solvent at ambient temperature to obtain a compound of formula (II), wherein all substitutions are described as earlier.

The above reaction is carried out in a solvent such as ethanol, tetrahydrofuran, toluene, ethyl acetate, water, titanium isopropoxide, dimethylformamide, dimethyl sulfoxide, dimethyl ether and the like or a mixture thereof and preferably using tetrahydrofuran. The reaction is carried by using reducing agents like sodium borohydride, lithium aluminium hydride, sodium cyanoborohyctride, and the like or a mixture thereof and preferably using lithium aluminium hydride. The reaction temperature may range from −20° C. to 10° C. based on the choice of solvent and preferably at a temperature in the range from −15° C. to 8° C. The duration of the reaction may range from 2 to 6 hours, preferably from a period of 3 to 5 hours. The compound of formula (II) is synthesized as described in preparation 2

Novel intermediate compound of general formula (III) is represented as given below, wherein all symbols are as defined earlier:

The present invention also provides a process for the preparation of a novel intermediate compound of general formula (III), which comprises of the following route:

The process of this invention includes, oxidation of compound of formula (II),

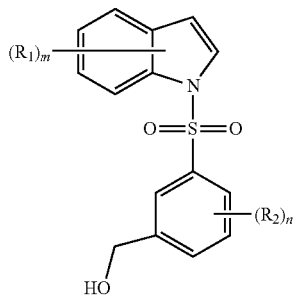

by using a suitable oxidizing agent in presence of inert solvent at ambient temperature to obtain compound of formula (III), wherein all substitutions are described as earlier.

The above reaction is carried out in a solvent such as tetrahydrofuran, toluene, ethyl acetate, ethylene dichloride, water, acetic acid, dimethylformamide, dimethyl sulfoxide, dimethyl ether and the like or a mixture thereof and preferably using ethylene dichloride. The reaction is carried by using oxidizing agents like hypochlorite, chlorate, nitric acid, chromium trioxide, chromate, dichromate, permanganate, manganate, manganese dioxide, peroxides and the like and preferably using manganese dioxide. The duration of the reaction may range from 2 to 6 hours, preferably from a period of 3 to 5 hours, wherein the compound of formula (II) is synthesized as described as earlier in specification.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out,
i) Converting a compound of the formula (I) into another compound of the formula (I)
ii) Removing any protecting groups; or
iii) Forming a pharmaceutically acceptable salt, solvate or a prodrug thereof.

Process (i) may be performed using conventional interconversion procedures such as epimerisation, oxidation, reduction, alkylation, nucleophilic or electrophilic aromatic substitution anclester hydrolysis or amide bond formation.

In process (ii) examples of protecting groups and the, means for their removal can be found in T. W. Greene 'Protective Groups in Organic Synthesis' (J. Wiley and Sons, 1991). Suitable amine protecting groups include sulfonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e. g. using an acid such as hydrochloric or trifluoroacetic acid) or reductively (e.g. hydrogenolysis of a benzyl group or reductive removal of a 2',2',2'-trichioroethoxycarbonyl, group using zinc in acetic acid) as appropriate. Other suitable amine protecting groups include trifluoroacetyl, which may be removed by base catalyzed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) halogenation, hydroxylation, alkylation and/or pharmaceutically acceptable salts may be prepared conventionally by reaction with the appropriate acid or acid derivative as described earlier in detail.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives-such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid);

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflators. In the case of a pressurized aerosol, a suitable propellant; e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule; it preferably should be in the form of powder. Capsules and cartridges (made, for example, from gelatin) for use in an inhaler or insufflator may be formulated containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average, adult human, for the treatment of the conditions referred to above, is 0.1 to 200 mg of the active ingredient per unit dose which could be administered, for example, 1 to 4 times per day.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift values are expressed in parts per million ($\delta$) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica-gel and executed under nitrogen pressure (flash chromatography) conditions.

EXAMPLES

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genus that is considered as the invention and any combination of the compounds or their moieties may itself form a genus. The following examples further illustrate details for the preparation of the compounds of the present invention. Those skilled in the art will readily understand that known variations of the conditions and process of the. following preparative procedures can be used to prepare these compounds.

Preparation 1: Preparation of 2-Bromo-5-(indole-1-sulfonyl) benzoic acid.

To a cooled (20° C.) suspension of sodium hydride (6.59 grams, 164.74 mmol) in 20 mL of THF, was added solution of indole (6.24 grams, 53.33 mmol in 25 mL tetrahydrofuran), slowly over a period of 10 minutes, maintaining mass temperature at 25° C. under nitrogen atmosphere. The mass was diluted with tetrahydrofuran (20 mL). The reaction mixture was further stirred for 1 hour at the same temperature. Then added a solution of 2-bromo-5-chlorosulfonyl benzoic acid (20.01 grams, 66.81 mmol) in tetrahydrofuran (30 mL) slowly over a period of 10 minutes., The progress of the reaction was monitored by thin layer chromatography (TLC). After completion of the reaction, the reaction mixture was quenched onto 600 mL cold Water. The reaction mass was acidified with conc. hydrochloric acid to pH 2 and extracted with ethyl acetate (2×200 mL). The combined organic layer was washed with brine solution (2×50 mL), water (2×100 mL), dried over anhydrous sodium sulphate and concentrated under reduced pressure to obtain 17.81 grams technical product. The material was used as such in the next step, with out further purification.

Melting Range: 188.7-191.4° C.;
I.R (cm$^{-1}$): 1710; 1683, 1579, 1440, 1371, 1255, 1180, 1124, 744;
$^1$H-NMR (ppm): 6.6-6.61 (1H, d, J=3.88 Hz), 7.13-7.24 (2H, m), 7.43-7.45 (2H, m), 7.61-7.64 (2H, m), 7.83-7.85 (1H, d, J=8.24), 8.23 (1H, d, J=2.04 Hz);
Mass (m/z): 378.1, 380.0 (M–H$^+$).

Preparation 2: Preparation of [2-Bromo-5-(indole-1-sulfonyl) phenyl] methanol.

To a suspension of Lithium aluminium hydride (2.3 grams, 60.5 mmol) in tetrahydrofuran (20 mL) was added a solution of 2-bromo-5-(indole-1-sulfonyl) benzoic acid (17.64 grams, 46.42 mmol) (obtained from preparation 1) in tetrahydrofuran (30 mL) maintaining mass temperature at 0-5° C. The reaction mass was stirred at 0-5° C. for 4 hours. The progress of the reaction was followed by TLC. After completion of the reaction, the reaction mass was cooled to −10° C. Water (20 mL) was added water slowly under nitrogen atmosphere. The reaction mass was diluted further with water (300 mL) and filtered through hyflow bed. The clear filtrate was extracted with ethyl acetate (4×100 mL). The combined organic layer was washed with brine solution (2×50 mL), water (2×50 mL) and dried over anhydrous sodium sulphate and was concentrated under reduced pressure. The residual mass was purified by column chromatography, the eluent system being ethyl acetate and hexane (2:8) to obtain 6.025 gram the title product.

Melting Range: 102.6-103.4° C.;
I.R (cm$^{-1}$): 3311, 1444, 1371, 1257, 1128, 879;
$^1$H-NMR (ppm): 4.69 (2H, s), 6.67-6.68 (11-1, dd, J=3.64, 0.68 Hz), 7.23-7.25 (1H, m), 7.32-7.33 (1H, m), 7.55-7.64 (4H, m), 7.97-7.99 (1H, dd, J=4.28, 0.8 Hz), 8.04-8.05 (11-1, d);
Mass (m/z): 366.0 (M+H)$^+$ Preparation 3: Preparation of 2-Bromo-5-(indole-1-sulfonyl) benzaldehyde.

To a solution of [2-Bromo-5-(indole-1-sulfonyl) phenyl] methanol (4.73 grams, 12.92 mmol) (obtained from preparation 2) in ethylene dichloride (75 mL) was added manganese dioxide (8.92 grams, 102.5 mmol). The reaction mass was heated to reflux temperature and maintained under reflux for 3 hours while monitoring the progress of the reaction by TLC. After completion of the reaction, the reaction mass was filtered through hyflow bed and the bed was washed with ethylene dichloride (2×10 mL). The clear filtrate was concentrated under reduced pressure to obtain technical product. The technical material was triturated with of n-hexane (2×15 mL), decanted the solvent and dried under reduced pressure to obtain 3.42 grams title product.

Melting Range: 106.4-107.9° C.;
I.R (cm$^{-1}$): 3074, 1691, 1571, 1440, 1371, 1253, 748;
$^1$H-NMR (ppm): 6.7-6.71 (1H, d, J=3.52 Hz), 7.23-7.36 (2H, m), 7.52-7.54 (2H, m), 7.71-7.73 (1H, d, J=8.4 Hz), 7.88-7.90 (1H, dd, J=8.44, 1.92 Hz), 7.96-7.98 (1H, d, J=8.28 Hz), 8.35-8.36 (1H, d, J=2.28 Hz), 10.27 (1H, s);
Mass (m/z): 364.0 (M+H)$^+$ Example 1

Preparation of 1-1-[4-Bromo-3-(4-ethyl piperazin-1-yl methyl) benzenesulfonyl]-1H-indole To a solution of 2-Bromo-5-(indole-1-sulfonyl) benzaldehyde (1.004 gram, 2.758 mmol) (obtained from preparation 3) in 20 mL ethylene dichloride was added N-ethyl piperazine (0.3757 gram, 3.295 mmol). Reaction mass was stirred at 25° C. for 10 minutes. Sodium triacetoxy borohydride (0.8842 gram, 4.171 mmol) was added over a period of 10 minutes. The reaction mass was stirred at 25° C. for 6 hours while monitoring the progress of the reaction by TLC. After completion of the reaction, reaction mass was quenched onto 5% sodium bicarbonate solution (100 mL) and extracted the product with chloroform (3×50 mL).

The combined organic layer was washed with brine solution (2×50 mL), water (2×50 mL) and dried over anhydrous sodium sulphate and concentrated under reduced pressure. The technical product was purified by column chromatography, eluent system being ethyl acetate and n-Hexane (7:1) to obtain 0.9344 gram title product.

Melting Range: 122.2-126.3° C.;
IR spectra (cm$^{-1}$): 3429, 2935, 2245, 1440, 1172, 765;
$^1$H-NMR (ppm): 1.20-1.24 (3H, t), 2.83 (4H, bs), 3.10-3.15 (21-1, q), 3.18 (4H, bs), 3.91 (2H, s), 6.75 (1H,=3.70 Hz), 7.21 (11-1, m), 7.28-7.30 (1H, m), 7.53-7.55 (114, d, J=7.7 Hz), 7.58-7.59 (1H, d, J=3.72 Hz), 7.69 (2H, m), 7.78 (1H, d, J=1.8 Hz), 7.9 (1H, d, J=8.2 Hz);
Mass (m/z): 462.1 (M+H)$^+$ Examples 2-11

The compounds of Examples 2-11 were prepared by following the procedure as described in Example 1, with some non-critical variations

| | |
|---|---|
| 2. 1-[4-Bromo-3-(4-methyl piperazin-1-yl methyl) benzenesulfonyl]-5-methoxy-1H-indole. | Melting Range: 115.2-120° C.; I.R (cm$^{-1}$): 2929, 1606, 1371, 1217, 817; $^1$H-NMR (ppm): 2.33 (3H, s), 2.35 (8H, bs), 3.50 (2H, bs), 3.80 (3H, s), 6.58 (1H, dd, J = 3.6, 0.48 Hz), 6.9 (1H, dd, J = 8.97, 2.50 Hz), 6.95 (1H, d, J = 2.43 Hz), |

| | |
|---|---|
| | 7.48 (1H, d, J = 3.6 Hz), 7.56 (2H, m), 7.85 (1H, d, J = 8.9 Hz), 7.96 (1H, d, J = 1.33 Hz); Mass (m/z): 477.9 (M + H)⁺. |
| 3. 1-[4-Bromo-3-(4-ethyl piperazin-1-yl methyl) benzenesulfonyl]-5-methoxy-1H-indole | Melting Range: 196.1-198.6° C.; I.R (cm⁻¹): 3444, 2430, 1614, 1438, 1224, 761; ¹H-NMR (ppm): 1.22-1.27 (3H, t), 2.65-2.66 (4H, bs), 2.99-3.00 (2H, bs), 3.12-3.14 (2H, bs), 3.22-3.34 (2H, q), 3.35-3.37 (2H, bs), 3.79 (3H, s), 6.67-6.79 (1H, d, J = 3.69 Hz), 6.93-6.96 (1H, dd, J = 9.01, 2.52 Hz), 7.10-7.11 (1H, d, J = 2.4 Hz), 7.71-7.72 (1H, dd, J = 8.45, 2.42 Hz), 7.75-7.76 (1H, d, J = 3.65 Hz), 7.80-7.85 (2H, m), 8.03 (1H, bs); Mass (m/z): 491.9 (M + H)⁺. |
| 4. 1-[4-Bromo-3-(4-ethyl piperazin-1-yl methyl) benzenesulfonyl]-5-fluoro-1H-indole. | Melting Range: 92.2-93.9° C.; I.R (cm⁻¹): 2939, 1589, 1458, 1138, 808; ¹H-NMR (ppm): 1.11 (3H, t), 2.43-2.48 (10H, bs), 3.51 (2H, s), 6.62-6.63 (1H, dd, J = 3.59, 0.44 Hz), 7.00-7.05 (1H, m), 7.16-7.19 (1H, dd, J = 8.66, 2.5 Hz), 7.5-7.6 (3H, m), 7.91-7.95 (1H, m), 7.97 (1H, d, J = 1.94 Hz); Mass (m/z): 479.8 (M + H)⁺. |
| 5. 1-[4-Chloro-3-(4-methyl piperazin-1-yl methyl) benzenesulfonyl]-5-fluoro-3-bromo-1H-indole. | Melting Range: 161.3-162.6° C.; I.R (cm⁻¹): 2804, 1589, 1465, 1159, 844; ¹H-NMR (ppm): 2.36 (3H, s), 2.41 (8H, bs), 3.54 (2H, s), 7.09-7.17 (2H, m), 7.41-7.43 (1H, d, J = 8.44 Hz), 7.64 (1H, s), 7.66-7.68 (1H, dd, J = 8.44, 2.48 Hz), 7.90-7.96 (1H, dd, J = 9.02, 4.12 Hz), 8.00-8.01 (1H, d, J = 2.32 Hz); Mass (m/z): 500.3 (M + H)⁺. |
| 6. 5-Isopropoxy-1-[3-(4-methyl piperazin-1-yl methyl) benzenesulfonyl]-1H-indole. | I.R (cm⁻¹): 2974, 1612, 1455, 1221, 923; ¹H-NMR (ppm): 1.31-1.32 (6H, d), 2.30 (3H, s), 2.46 (8H, bs), 3.47 (2H, s), 4.47 (1H, m), 6.55-6.56 (1H, d, J = 3.56 Hz), 6.87-6.90 (1H, dd, J = 8.96, 2.44 Hz), 6.95-6.96 (1H, d, J = 2.44 Hz), 7.33-7.37 (1H, m), 7.45-7.47 (1H, m), 7.50-7.51 (1H, d, J = 3.56 Hz), 7.7-7.72 (1H, m), 7.84-7.87 (2H, m); Mass (m/z): 428.3 (M + H)⁺. |
| 7. 4-Chloro-1-[3-(4-methyl piperazin-1-yl methyl) benzenesulfonyl]-1H-indole. | I.R (cm⁻¹): 3144, 2937, 1602, 1463, 1287, 895; ¹H-NMR (ppm): 2.3 (3H, s), 2.36 (8H, bs), 3.48 (2H, s), 6.77-6.79 (1H, dd, J = 3.72, 0.68 Hz), 7.21-7.23 (2H, m), 7.37-7.40 (1H, m), 7.48 (1H, m), 7.61-7.62 (1H, d, J = 3.72 Hz), 7.73 (1H, m), 7.85 (1H, m), 7.89-7.9 (1H, m); Mass (m/z): 404.3 (M + H)⁺. |
| 8. 1-[3-(4-Methyl piperazin-1-yl methyl) benzenesulfonyl]-1H-indole. | I.R (cm⁻¹): 2936, 1445, 1168, 823; ¹H-NMR (ppm): 2.29 (3H, s), 2.36 (8H, bs), 3.47 (2H, s), 6.65-6.66 (d, 1H, d, J = 3.68 Hz), 7.19-7.23 (1H, m), 7.30 (1H, m), 7.36-7.38 (1H, m), 7.45-7.53 (2H, m), 7.56-7.57 (1H, d, J = 3.68 Hz), 7.73-7.75 (1H, m), 7.87 (1H, m), 7.98-8.00 (1H, d, J = 8.32 Hz); Mass (m/z): 370.3 (M + H)⁺. |
| 9. 5-Methoxy-1-[3-(4-methyl piperazin-1-yl methyl) benzenesulfonyl]-1H-indole. | I.R (cm⁻¹): 2936, 2790, 1615, 1465, 1224, 996; ¹H-NMR (ppm): 2.28 (3H, s), 2.35 (8H, bs), 3.46 (2H, s), 3.80 (3H, s), 6.57-6.58 (1H, d, J = 3.6 Hz), 6.89-6.92 (1H, dd, J = 8.96, 2.52 Hz), 6.95 (1H, d, J = 2.44 Hz), 7.33-7.36 (1H, m), 7.45-7.47 (1H, m), 7.51-7.52 (1H, d, J = 3.6 Hz), 7.69-7.71 (1H, m), 7.83 (1H, s), 7.86-7.89 (1H, d, J = 9.0 Hz); Mass (m/z): 400.3 (M + H)⁺. |
| 10. 5-Fluoro-1-[3-(4-methyl piperazin-1-yl methyl) benzenesulfonyl]-1H-indole. | I.R (cm⁻¹): 2937, 1590, 1460, 1216, 998; ¹H-NMR (ppm): 2.30 (3H, s), 2.36 (8H, bs), 3.48 (2H, s), 6.61-6.62 (1H, d, J = 3.64 Hz), 7.03 (1H, m), 7.15-7.18 (1H, m), 7.37-7.39 (1H, m), 7.47 (1H, m), 7.59-7.60 (1H, d, = 3.64 Hz), 7.71 (1H, m), 7.84 (1H, m), 7.92-7.94 (1H, m); Mass (m/z): 388.3 (M + H)⁺. |
| 11. 5-Ethoxy-1-[3-(4-methyl piperazin-1-yl methyl) benzenesulfonyl]-1H-indole. | I.R (cm⁻¹): 3743, 2935, 1615, 1456, 1222, 900; ¹H-NMR (ppm): 1.38-1.42 (3H, t), 2.28 (3H, s), 2.35 (8H, bs), 3.48 (2H, s), 3.98-4.03 (2H, q), 6.56-6.57 (1H, d, J = 3.60 Hz), 6.89-6.92 (1H, dd, J = 8.96, 2.45 Hz), 6.93-6.94 (1H, d, J = 2.38 Hz), 7.32-7.36 (1H, m), 7.44-7.46 (1H, m), 7.50-7.51 (1H, d, J = 3.64 Hz), 7.69-7.71 (1H, m), 7.83 (1H, s), 7.86-7.88 (1H, d, J = 8.98 Hz). Mass (m/z): 414.4 (M + H)⁺. |

Example 12

Preparation of 1-1-[4-Bromo-3-(4-ethyl piperazin-1-yl methyl) benzenesulfonyl]-1H-indole dihydrochloride

To a clear solution of 1- [4-Bromo-3-(4-ethyl piperazin-1yl-methyl) benzenesulfonyl]-1H-indole (252.4 mg, 0.5463 mmol) (obtained from example 1) in diethyl ether (15 mL) under nitrogen atmosphere, added a solution of methanolic hydrochloric acid (16% w/v, 0.32 mL, 1.402 mmol) in 5 minutes under stirring. The above reaction mass was further stirred at 25° C., for a period of 1 hour and concentrated under vacuum to obtain the above title product.

Melting Range: 208.4-210.4° C.
IR spectra (cm$^{-1}$): 3429, 2935, 2245, 1440, 1172, 765;
$^1$H-NMR (ppm): 1.20-1.24 (3H, t), 2.83 (4H, bs), 3.10-3.15 (2H, q), 3.18 (4H, bs), 3.91 (2H, s), 6.75 (1H, d, J=3.70 Hz), 7.21 (1H, m), 7.28-7.30 (1H, m), 7.53-7.55 (1H, d, J=7.7 Hz), 7.58-7.59 (1H, d, J=3.72 Hz), 7.69 (2H, m), 7.78 (1H, d, J=1.8 Hz), 7.9 (1H, d, J=8.2 Hz);
Mass (m/z): 461.9 (M+H)$^+$

Examples 13-46

The compounds of Examples 13-46 were prepared by following the procedure as described in Example 12, with some non-critical variations

| | | |
|---|---|---|
| 13. | 1-[4-Chloro-3-(4-methyl piperazin-1-yl methyl) benzenesulfonyl]-1H-indole dihydrochloride. | Melting Range: 210.6-213.90° C.; I.R (cm$^{-1}$): 3415, 2987, 1591, 1444, 1373, 1174, 736; $^1$H-NMR (ppm): 2.84 (3H, s), 3.05 (4H, bs), 3.28 (4H, bs), 4.10 (2H, s), 6.72-6.78 (1H, d, J = 3.7 Hz), 7.18-7.22 (1H, d, J = 7.4 Hz), 7.26-7.30 (1H, d, J = 7.4 Hz), 7.49-7.51 (2H, d, J = 8.4 Hz), 7.55-7.56 (1H, d, J = 3.72 Hz), 7.82-7.84 (1H, dd, J = 8.52, 2.32 Hz), 7.86-7.88 (2H, dd, J = 7.92, 2.06 Hz); Mass (m/z): 403.9 (M + H)$^+$. |
| 14. | 1-[4-Chloro-3-(4-methyl piperazin-1-yl methyl) benzenesulfonyl]-5-fluoro-1H-indole dihydrochloride. | Melting Range: 220.2-221.3° C.; I.R (cm$^{-1}$): 3429, 2983, 1591, 1463, 1377, 1138, 950; $^1$H-NMR (ppm): 2.84 (3H, s), 3.05 (4H, bs), 3.34-3.36 (4H, bs), 3.98 (2H, s), 6.60-6.61 (1H, d, J = 3.67), 6.91-6.96 (1H, m, J = 9.18, 2.4 Hz), 7.04-7.07 (1H, dd, J = 8.99, 2.41 Hz), 7.26-7.28 (1H, d, J = 8.52 Hz), 7.53-7.54 (1H, d, J = 3.68 Hz), 7.63-7.66 (1H, dd, J = 8.5, 1.9 Hz), 7.72-7.75 (1H, m, J = 4.34 Hz), 7.85-7.86 (1H, d, J = 2.18 Hz); Mass (m/z): 422.0 (M + H)$^+$. |
| 15. | 1-[4-Chloro-3-(4-ethyl piperazin-1-yl methyl) benzenesulfonyl]-1H-indole dihydrochloride. | Melting Range: 196.0-197.1° C.; I.R (cm$^{-1}$): 3446, 2985, 2451, 1469, 1444, 1172, 740; $^1$H-NMR (ppm): 1.17-1.21 (3H, t), 3.04 (8H, bs), 3.10-3.15 (2H, q), 4.10 (2H, s), 6.69-6.70 (1H, d, J = 3.61 Hz), 7.15-7.19 (1H, m, J = 7.5 Hz), 7.23-7.27 (1H, m, J = 7.3 Hz), 7.46-7.48 (2H, d, J = 8.34 Hz), 7.52-7.53 (1H, d, J = 3.71 Hz), 7.79-7.81 (1H, dd, J = 8.5, 2.2 Hz), 7.84-7.86 (2H, m); Mass (m/z): 418.0 (M + H)$^+$. |
| 16. | 1-[4-Chloro-3-(4-methyl piperazin-1-yl methyl) benzenesulfonyl]-5-methoxy-1H-indole dihydrochloride. | Melting Range: 208.8-210.2° C.; I.R (cm$^{-1}$): 3446, 2981, 2372, 1585, 1465, 1222, 952; $^1$H-NMR (ppm): 2.82 (3H, s), 3.05 (4H, bs), 3.23-3.28 (4H, bs), 3.60 (3H, s), 3.9 (2H, s), 6.55-6.56 (1H, d, J = 3.64 Hz), 6.67-6.79 (1H, dd, J = 9.03, 2.44 Hz), 6.88-6.89 (1H, d, J = 2.42 Hz), 7.20-7.22 (1H, d, J = 8.53 Hz), 7.42-7.43 (1H, d, J = 3.65 Hz), 7.58-7.61 (1H, dd, J = 8.5, 2.1 Hz), 7.65-7.68 (1H, d, J = 9.04 Hz), 7.79 (1H, d, J = 2.21 Hz); Mass (m/z): 434.1 (M + H)$^+$. |
| 17. | 1-[4-Chloro-3-(4-methyl piperazin-1-yl methyl) benzenesulfonyl]-5-bromo-1H-indole dihydrochloride. | Melting Range: 214.7-215.6° C.; I.R (cm$^{-1}$): 3444, 2953, 1444, 1134, 952; $^1$H-NMR (ppm): 2.8 (7H, bs), 3.2 (4H, bs), 3.93 (2H, bs), 6.64 (1H, bs), 7.37-7.54 (4H, m), 7.79 (3H, bs); Mass (m/z): 481.9 (M + H)$^+$. |
| 18. | 1-[4-Chloro-3-(4-ethyl piperazin-1-yl methyl) benzenesulfonyl]-5-methoxy-1H-indole dihydrochloride. | Melting Range: 209.5-211.0° C.; I.R (cm$^{-1}$): 3448, 2983, 1585, 1465, 1222, 761; $^1$H-NMR (ppm): 1.19-1.23 (3H, t), 2.97 (4H, bs), 3.11-3.16 (2H, q), 3.23 (4H, bs), 3.67 (3H, s), 4.0 (2H, bs), 6.61-6.62 (1H, d, J = 3.66 Hz), 6.83-6.86 (1H, dd, J = 9.0, 2.5 Hz), 6.98 (1H, d, J = 2.47 Hz), 7.39-7.41 (1H, d, J = 8.54 Hz), 7.46-7.47 (1H, d, J = 3.68 Hz), 7.71-7.74 (2H, m), 7.80 (1H, d, J = 2.2 Hz); Mass (m/z): 448.0 (M + H)$^+$. |

| | |
|---|---|
| 19. 1-[4-Chloro-3-(4-ethyl piperazin-1-yl methyl) benzenesulfonyl]-4-chloro-1H-indole dihydrochloride. | Melting Range: 205.9-207.2° C.;<br>I.R (cm$^{-1}$): 3450, 2981, 2376, 1624, 1460, 1168, 893;<br>$^1$H-NMR (ppm): 1.16-1.19 (3H, t), 2.79 (4H, bs), 3.06-3.11 (2H, q), 3.20 (4H, bs), 3.62 (2H, bs), 6.71-6.72 (1H, d, J = 3.67 Hz), 7.11-7.16 (2H, m), 7.34-7.36 (1H, d, J = 8.8 Hz), 7.56-7.57 (1H, d, J = 3.76 Hz), 7.70-7.73 (2H, m), 7.75-7.76 (1H, d, J = 2.52 Hz);<br>Mass (m/z): 451.9 (M + H)$^+$. |
| 20. 1-[4-Chloro-3-(4-methyl piperazin-1-yl methyl) benzenesulfonyl]-4-chloro-1H-indole dihydrochloride. | Melting Range: 242.7-244.3° C.;<br>I.R (cm$^{-1}$): 3446, 2983, 2650, 1647, 1465, 1282, 891;<br>$^1$H-NMR (ppm): 2.78 (7H, bs), 3.2 (4H, bs), 3.74 (2H, bs), 6.65-6.66 (1H, d, J = 3.59 Hz), 7.04-7.12 (2H, m), 7.21-7.23 (1H, d, J = 8.25 Hz), 7.52-7.53 (1H, d, J = 3.70 Hz), 7.60-7.62 (1H, d, J = 8.24 Hz), 7.68-7.70 (1H, d, J = 8.10 Hz), 7.76-7.77 (1H, d, J = 2.02 Hz);<br>Mass (m/z): 437.9 (M + H)$^+$. |
| 21. 1-[4-Bromo-3-(4-methyl piperazin-1-yl methyl) benzenesulfonyl]-1H-indole dihydrochloride. | Melting Range: 214.1-216.0° C.;<br>I.R (cm$^{-1}$): 3429, 2372, 1440, 1170, 740;<br>$^1$H-NMR (ppm): 2.26 (2H, bs), 2.79 (5H, s), 3.09-3.11 (2H, bs), 3.37-3.40 (2H, bs), 3.7 (2H, s), 6.86 (1H, dd, J = 3.7, 0.57 Hz), 7.24-7.28 (1H, m), 7.33-7.37 (1H, m), 7.59-7.61 (1H, d, J = 7.67 Hz), 7.76-7.78 (1H, dd, J = 8.4, 2.4 Hz), 7.80-7.81 (1H, d, J = 3.6 Hz), 7.84-7.86 (1H, d, J = 8.44 Hz), 7.93-7.95 (1H, dd, J = 8.0, 0.35 Hz), 8.09 (1H, bs);<br>Mass (m/z): 447.9 (M + H)$^+$. |
| 22. 1-[4-methyl-3-(4-methyl piperazin-1-yl methyl) benzenesulfonyl]-1H-indole dihydrochloride. | Melting Range: 180.4-183.0° C.;<br>I.R (cm$^{-1}$): 3383, 2960, 1629, 1446, 1130, 948;<br>$^1$H-NMR (ppm): 2.45 (3H, s), 2.97 (3H, s), 3.29-3.58 (8H, bs), 4.25 (2H, s), 6.72-6.73 (1H, dd, J = 3.69, 0.39 Hz), 7.20-7.24 (1H, m), 7.31-7.35 (1H, m), 7.41-7.43 (1H, d, J = 8.18 Hz), 7.52-7.54 (1H, d, J = 7.8 Hz), 7.67-7.68 (1H, d, J = 3.68 Hz), 7.83-7.85 (1H, dd, J = 8.14, 2.02 Hz), 8.02-8.04 (1H, dd, J = 8.28, 0.52 Hz), 8.12 (1H, d, J = 1.24 Hz);<br>Mass (m/z): 384.6 (M + H)$^+$. |
| 23. 1-[4-methyl-3-(4-ethyl piperazin-1-yl methyl) benzenesulfonyl]-1H-indole dihydrochloride. | Melting Point: 250.13° C.;<br>I.R (cm$^{-1}$): 3300, 2997, 1643, 1168, 752;<br>$^1$H-NMR (ppm): 1.35-1.39 (3H, t), 2.42 (3H, s), 3.12-3.14 (6H, bs), 3.23-3.29 (2H, q), 3.6 (2H, bs), 4.05 (2H, bs), 6.72-6.73 (1H, dd J = 3.12, 0.58 Hz), 7.20-7.24 (1H, m), 7.30-7.34 (1H, m), 7.38-7.40 (1H, d, J = 8.17 Hz), 7.52-7.54 (1H, d, J = 7.82 Hz), 7.65-7.66 (1H, d, J = 3.69 Hz), 7.80-7.82 (1H, dd, J = 8.11, 1.97 Hz), 8.0-8.02 (2H, m);<br>Mass (m/z): 398.1 (M + H)$^+$. |
| 24. 1-[4-methyl-3-(4-methyl piperazin-1-yl methyl) benzenesulfonyl]-5-methoxy-1H-indole dihydrochloride. | Melting Range: 198.1-199.3° C.;<br>I.R (cm$^{-1}$): 3427, 2974, 2372, 1616, 1465, 1224, 950;<br>$^1$H-NMR (ppm): 2.37 (3H, s), 2.78 (3H, s), 2.79-3.46 (8H, bs), 3.73 (3H, s), 3.83-3.90 (2H, bs), 6.73-6.74 (1H, d, J = 3.6 Hz), 6.91-6.93 (1H, dd, J = 9.01, 2.5 Hz), 7.08 (1H, d, J = 2.46 Hz), 7.39-7.41 (1H, d, J = 8.13 Hz), 7.73-7.76 (2H, m), 7.82-7.84 (1H, d, J = 9.02 Hz), 8.11 (1H, bs);<br>Mass (m/z): 414.3 (M + H)$^+$. |
| 25. 1-[4-Chloro-3-(4-ethyl piperazin-1-yl methyl) benzenesulfonyl]-5-fluoro-1H-indole dihydrochloride. | Melting Range: 204.1-205.5° C.;<br>I.R (cm$^{-1}$): 3414, 2976, 1622, 1458, 1139, 804;<br>$^1$H-NMR (ppm): 1.20-1.23 (3H, t), 3.04 (4H, bs), 3.13-3.18 (2H, q), 3.32-3.34 (4H, bs), 4.05 (2H, s), 6.65-6.66 (1H, d, J = 3.67 Hz), 6.99-7.03 (1H, m), 7.13-7.16 (1H, dd, J = 9.0, 2.5 Hz), 7.41-7.43 (1H, d, J = 8.55 Hz), 7.56-7.57 (1H, d, J = 3.7 Hz), 7.74-7.76 (1H, dd, J = 8.55, 2.26 Hz), 7.78-7.81 (1H, dd, J = 9.0, 4.1 Hz), 7.86 (1H, d, J = 2.3 Hz);<br>Mass (m/z): 436.0 (M + H)$^+$. |
| 26. 1-[4-Bromo-3-(4-methyl piperazin-1-yl methyl) benzenesulfonyl]-5-fluoro-1H-indole dihydrochloride. | Melting Range: 219.4-221.6° C.;<br>I.R (cm$^{-1}$): 3435, 2924, 2366, 1633, 1452, 1134, 943;<br>$^1$H-NMR (ppm): 2.83 (3H, s), 2.93 (4H, bs), 3.2-3.26 (4H, bs), 3.96 (2H, s), 6.70-6.71 (1H, d, J = 3.6 Hz), |

| | |
|---|---|
| | 7.02-7.07 (1H, m), 7.19-7.22 (1H, dd, J = 9.02, 2.5 Hz), 7.6-7.62 (1H, d, J = 3.72 Hz), 7.67-7.72 (2H, bs), 7.8 (1H, s), 7.82-7.86 (1H, m); Mass (m/z): 465.7 (M + H)+. |
| 27. 1-[4-Bromo-3-(4-methyl piperazin-1-yl methyl) benzenesulfonyl]-5-methoxy-3-methyl-1H-indole dihydrochloride. | Melting Range: 214.3-215.7° C.; I.R (cm−1): 3429, 2426, 1610, 1446, 1172, 881; 1H-NMR (ppm): 2.16 (3H, s), 2.65 (2H, bs) 2.69 (3H, s), 2.77 (2H, bs), 2.8 (2H, bs), 3.3 (2H, bs), 3.76 (2H, bs), 3.8 (3H, s), 6.92-6.95 (1H, dd, J = 8.96, 2.5 Hz), 7.01-7.02 (1H, d, J = 2.45 Hz), 7.53 (1H, d, J = 1.17 Hz), 7.66-7.69 (1H, dd, J = 8.44, 2.4 Hz), 7.79-7.83 (2H, m), 8.04 (1H, bs); Mass (m/z): 492.3 (M + H)+. |
| 28. 1-[4-Bromo-3-(4-ethyl piperazin-1-yl methyl) benzenesulfonyl]-5-methoxy-3-methyl-1H-indole dihydrochloride. | Melting Range: 211.3-212.1° C.; I.R (cm−1): 3442, 2947, 2376, 1610, 1172, 883; 1H-NMR (ppm): 1.27 (3H, t), 2.16 (3H, s), 2.81 (4H, bs), 2.87 (2H, bs), 3.06 (2H, bs), 3.35 (2H, q) 3.70 (2H, s), 3.8 (3H, s), 6.93-6.96 (1H, dd, J = 8.96, 2.50 Hz), 7.01-7.02 (1H, d, J = 2.46 Hz), 7.53 (1H, d, J = 1.13 Hz), 7.67-7.7 (1H, dd, J = 8.44, 2.38 Hz), 7.80-7.84 (2H, m), 8.07 (1H, bs); Mass (m/z): 506.0 (M + H)+. |
| 29. 1-[4-Chloro-3-(4-ethyl piperazin-1-yl methyl) benzenesulfonyl]-5-bromo-1H-indole dihydrochloride. | Melting Range: 208.6-212.8° C.; I.R (cm−1): 3425, 2976, 1566, 1165, 960; 1H-NMR (ppm): 1.19-1.23 (3H, t), 2.91 (4H, bs), 3.14-3.15 (2H, q), 3.4-3.47 (4H, bs), 3.98 (2H, bs), 6.57 (1H, bs), 7.27 (2H, bs), 7.47 (2H, bs), 7.68 (2H, bs), 7.93 (1H, bs); Mass (m/z): 496.2 (M + H)+. |
| 30. 1-[4-Chloro-3-(4-ethyl piperazin-1-yl methyl) benzenesulfonyl]-5-methoxy-3-methyl-1H-indole dihydrochloride. | Melting Range: 217.5-220.8° C.; I.R (cm−1): 3456, 2983, 1612, 1448, 1172, 962; 1H-NMR (ppm): 1.10-1.14 (3H, t), 1.91 (3H, bs), 3.07-3.12 (10H, bs), 3.60 (3H, s), 4.18 (2H, s), 6.74-6.8 (2H, m), 7.11 (1H, s), 7.37-7.39 (1H, d, J = 8.76 Hz), 7.61-7.67 (2H, m), 7.74 (1H, s); Mass (m/z): 462.2 (M + H)+. |
| 31. 1-[4-Chloro-3-(4-methyl piperazin-1-yl methyl) benzenesulfonyl]-5-methoxy-3-methyl-1H-indole dihydrochloride. | Melting Range: 213.3-214.2° C.; I.R (cm−1): 3479, 2963, 2441, 1608, 1454, 1172, 883; 1H-NMR (ppm): 2.16 (3H, s), 2.77 (3H, s), 2.95-2.99 (6H, bs), 3.45 (2H, bs), 3.94 (3H, s), 4.29 (2H, bs), 6.92-6.96 (1H, dd, J = 8.96, 2.52 Hz), 7.01 (1H, d, J = 2.44 Hz), 7.54 (1H, d, J = 1.04 Hz), 7.66-7.68 (1H, d, J = 8.52 Hz), 7.79-7.83 (2H, m), 8.22 (1H, s); Mass (m/z): 448.3 (M + H)+. |
| 32. 1-[4-Chloro-3-(4-methyl piperazin-1-yl methyl) benzenesulfonyl]-5-methoxy-3-bromo-1H-indole dihydrochloride. | Melting Range: 195.4-199.3° C.; I.R (cm−1): 3421, 2368, 1465, 1166, 956; 1H-NMR (ppm): 2.77 (3H, s) 3.09-3.39 (8H, bs), 3.49 (2H, s), 3.96 (3H, s), 6.88 (2H, d, J = 2.08 Hz), 7.03-7.06 (1H, dd, J = 9.02, 1.6 Hz), 7.69-7.73 (1H, d, J = 8.8 Hz), 7.88-7.90 (2H, d, J = 9.0 Hz), 8.12-8.23 (1H, bs); Mass (m/z): 512.4 (M + H)+. |
| 33. 1-[4-Chloro-3-(4-ethyl piperazin-1-yl methyl) benzenesulfonyl]-5-methoxy-3-bromo-1H-indole dihydrochloride. | Melting Range: 216.9-219.7° C.; I.R (cm−1): 3419, 1624, 1166, 958; 1H-NMR (ppm): 1.24-1.27 (3H, t), 2.85 (4H, bs), 2.95 (4H, bs), 3.45 (2H, q), 3.79 (3H, s), 4.1 (2H, s), 6.88-6.89 (1H, d, J = 2.48 Hz), 7.04-7.07 (1H, dd, J = 8.04, 2.52 Hz), 7.71-7.73 (1H, d, J = 8.48 Hz), 7.90-7.93 (2H, m), 8.12 (1H, s), 8.24-8.31 (1H, m); Mass (m/z): 526.4 (M + H)+. |
| 34. 1-[4-Chloro-3-(4-ethyl piperazin-1-yl methyl) benzenesulfonyl]-3-methyl-1H-indole dihydrochloride. | Melting Range: 218.9-220.5° C.; I.R (cm−1): 3417, 2436, 1631, 1442, 1166, 966; 1H-NMR (ppm): 1.19-1.22 (3H, t), 2.00 (3H, s), 2.93 (4H, bs) 3.11-3.16 (2H, q), 3.33-3.35 (4H, bs), 4.01 (2H, bs), 7.10-7.14 (1H, m), 7.23-7.30 (4H, m), 7.61 (1H, d, J = 8.64, 1.74 Hz), 7.82-7.84 (2H, m); Mass (m/z): 432.3 (M + H)+. |
| 35. 1-[4-Chloro-3-(4-methyl piperazin-1-yl methyl) benzenesulfonyl]-3-methyl-1H-indole dihydrochloride. | Melting Range: 216.9-218.7° C.; I.R (cm−1): 3493, 2673, 1627, 1450, 1174, 962; 1H-NMR (ppm): 2.01 (3H, s), 2.83 (3H, s), 3.00 (4H, bs), 3.2-3.35 (4H, bs); 3.98 (2H, s), 7.12-7.14 (1H, m), 7.15-7.31 (4H, m), |

| | | |
|---|---|---|
| | | 7.62-7.63 (1H, dd, J = 8.54, 1.96 Hz), 7.65-7.84 (2H, m); Mass (m/z): 418.4 (M + H)⁺. |
| 36. | 1-[4-Bromo-3-(4-methyl piperazin-1-yl methyl) benzenesulfonyl]-5-bromo-1H-indole dihydrochloride. | Melting Range: 208.2-209.2° C.; I.R (cm⁻¹): 3436, 2360, 1441, 1171, 950; ¹H-NMR (ppm) 2.59 (4H, bs), 2.77 (3H, s), 3.12 (2H, bs), 3.22 (2H, bs), 3.83 (2H, s), 6.49-6.50 (1H, d, J = 3.45 Hz), 7.13 (2H, m), 7.31 (2H, m), 7.49 (1H, d, J = 3.53 Hz); 7.59 (1H, d, J = 8.94 Hz), 7.69 (1H, s); Mass (m/z): 526.3 (M+ H)⁺. |
| 37. | 1-[4-Bromo-3-(4-ethyl piperazin-1-yl methyl) benzenesulfonyl]-5-bromo-1H-indole dihydrochloride. | Melting Range: 205.1-207.1° C.; I.R (cm⁻¹): 3435, 2346, 1439, 1172, 815; ¹H-NMR (ppm): 1.07-1.22 (3H, t), 2.59-2.89 (6H, bs), 3.04-3.07 (2H, q), 3.10-3.12 (2H, bs), 3.34 (2H, s), 6.50-6.51 (1H, d, J = 3.39 Hz), 7.15 (2H, m), 7.32 (2H, m), 7.49 (1H, dd, J = 9.24, 3.49 Hz), 7.61 (1H, d, J = 8.74 Hz), 7.70 (1H, bs); Mass (m/z): 540.2 (M + H)⁺. |
| 38. | 1-[4-Bromo-3-(4-methyl piperazin-1-ylmethyl) benzenesulfonyl]-3-methyl-1H-indole dihydrochloride. | Melting Range: 210.5-213° C.; I.R (cm⁻¹): 3429, 2370, 1631, 1174, 948; ¹H-NMR (ppm): 1.97 (3H, s), 2.79 (7H, bs), 3.10-3.17 (4H, bs), 3.72 (2H, s), 7.06-7.08 (1H, m), 7.17-7.21 (4H, m), 7.37 (1H, m), 7.72 (1H, bs), 7.79-7.82 (1H, d, J = 8.20 Hz); Mass (m/z): 462.2 (M + H)⁺. |
| 39. | 1-[4-Bromo-3-(4-ethyl piperazin-1-yl methyl) benzenesulfonyl]-3-methyl-1H-indole dihydrochloride. | Melting Range: 204.1-206.5° C.; I.R (cm⁻¹): 3439, 2434, 1566, 1442, 1174, 966; ¹H-NMR (ppm): 1.16-1.19 (3H, t), 1.96 (3H, s), 2.77-2.94 (4H, bs), 3.04 (2H, q), 3.08 (4H, bs), 3.69 (2H, s), 7.04-7.20 (4H, m), 7.22 (1H, bs), 7.35-7.37 (1H, d, J = 8.2 Hz), 7.72 (1H, bs), 7.8-7.82 (1H, d, J = 8.16 Hz); Mass (m/z): 476.2 (M + H)⁺. |
| 40. | 1-[4-Methyl-3-(4-ethyl piperazin-1-yl methyl) benzenesulfonyl]-5-methoxy-3-methyl-1H-indole dihydrochloride. | Melting Point: 226.99° C.; I.R (cm⁻¹): 3423, 2372, 1604, 1442, 1168, 885; ¹H-NMR (ppm): 1.09-1.13 (3H, t), 1.85 (3H, s), 2.00 (3H, s), 2.92 (8H, bs), 3.01-3.07 (2H, q), 3.54 (3H, s), 3.86 (2H, s), 6.65-6.68 (1H, dd, J = 8.91, 2.38 Hz), 6.69-6.70 (1H, d, J = 2.13 Hz), 6.96-6.99 (1H, d, J = 8.30 Hz), 7.06 (1H, s), 7.43-7.46 (1H, dd, J = 8.14, 1.53 Hz), 7.53-7.54 (1H, d, J = 1.7 Hz), 7.55-7.58 (1H, d, J = 8.85 Hz); Mass (m/z): 442.4 (M + H)⁺. |
| 41. | 1-[4-Methyl-3-(4-methyl piperazin-1-yl methyl) benzenesulfonyl]-5-methoxy-3-methyl-1H-indole dihydrochloride. | Melting Point: 190.32° C.; I.R (cm⁻¹): 3415, 2935, 1606, 1460, 1174, 958; ¹H-NMR (ppm): 1.90 (3H, s), 2.09 (3H, s), 2.76 (3H, s), 3.02 (8H, bs), 3.59 (3H, s), 3.97 (2H, s), 6.70-6.73 (1H, dd, J = 8.74, 2.08 Hz), 6.77 (1H, s), 7.11-7.13 (2H, d, J = 6.26 Hz), 7.52-7.60 (3H, m); Mass (m/z): 428.1 (M + H)⁺. |
| 42. | 1-[4-Methyl-3-(4-ethyl piperazin-1-yl methyl) benzenesulfonyl]-5-methoxy-1H-indole dihydrochloride. | Melting Point: 160.94° C.; I.R (cm⁻¹): 3408, 2987, 1620, 1136, 765; ¹H-NMR (ppm): 1.23-1.27 (3H, t), 2.37 (3H, s), 2.97-3.1 (8H, bs), 3.34-3.35 (2H, q), 3.83 (3H, s), 3.98 (2H, s), 6.74-6.75 (1H, d, J = 3.5 Hz), 6.91-6.94 (1H, dd, J = 9.01, 2.51 Hz), 7.08 (1H, d, J = 2.49 Hz), 7.39-7.41 (1H, d, J = 1.17 Hz), 7.73-7.76 (2H, m), 7.83-7.85 (1H, d, J = 9.02 Hz), 8.09 (1H, bs); Mass (m/z): 428.3 (M + H)⁺. |
| 43. | 1-[4-Methyl-3-(4-methyl piperazin-1-yl methyl) benzenesulfonyl]-5-fluoro-1H-indole dihydrochloride. | Melting Range: 220.3-223.4° C.; I.R (cm⁻¹): 3370, 2642, 1596, 1464, 1171, 949; ¹H-NMR (ppm): 2.45 (3H, s), 2.97 (3H, s), 3.29-3.62 (8H, bs), 4.19 (2H, s), 6.72-6.73 (1H, d, J = 3.6 Hz), 7.07-7.13 (1H, m), 7.23-7.25 (1H, dd, J = 8.9, 2.52 Hz), 7.41-7.43 (1H, d, J = 8.18 Hz), 7.75-7.76 (1H, d, J = 3.67 Hz), 7.82-7.89 (1H, dd, J = 8.14, 1.96 Hz), 8.01-8.02 (1H, m), 8.12 (1H, bs); Mass (m/z): 402.3 (M + H)⁺. |
| 44. | 1-[4-Methyl-3-(4-ethyl piperazin-1-yl methyl) benzenesulfonyl]-5-fluoro-1H-indole dihydrochloride. | Melting Range: 203.4-206.2° C.; I.R (cm⁻¹): 3425, 2458, 1594, 1443, 1171, 799; ¹H-NMR (ppm): 1.23-1.27 (3H, t), 2.38 (3H, s), 3.03-3.06 (8H, bs), 3.35-3.37 (2H, q), 3.8 (2H, bs), 6.81-6.82 (1H, d, J = 3.56 Hz), 7.16-7.21 (1H, m, J = 9.2, 2.62 Hz), 7.39-7.41 (1H, dd, J = 9.16, 2.58 Hz), 7.41-7.43 (1H, d, J = 7.86 Hz), 7.79-7.81 (1H, d, J = 6.98 Hz), 7.87-7.88 (1H, |

| | | |
|---|---|---|
| 45. | 1-[4-Chloro-3-(4-ethyl-[1,4]diazepan-1-yl methyl) benzenesulfonyl]-3-methyl-1H-indole dihydrochloride. | d, J = 3.66 Hz), 7.94-7.98 (1H, m, J = 9.02, 4.42 Hz), 8.13 (1H, bs); Mass (m/z): 416.3 (M + H)$^+$. I.R (cm$^{-1}$): 3441, 2946, 1608, 1445, 1119, 973; $^1$H-NMR (ppm): 1.12-1.16 (3H, t), 1.93-1.98 (2H, m), 2.00 (3H, s), 2.92-2.96 (2H, m), 3.05-3.07 (2H, q), 3.11-3.28 (4H, m), 3.38 (2H, bs), 4.11 (2H, s), 7.03-7.07 (1H, m), 7.11-7.15 (1H, m), 7.21 (1H, s), 7.26-7.28 (1H, d, J = 7.72 Hz), 7.40-7.42 (1H, d, J = 8.52 Hz), 7.66-7.69 (1H, dd, J = 8.50, 2.11 Hz), 7.77-7.79 (1H, d, J = 8.26 Hz), 8.05 (1H, d, J = 1.80 Hz); Mass (m/z): 446.3 (M + H)$^+$. |
| 46. | 1-[4-Chloro-3-(4-methyl[1,4]diazepan-1-yl methyl) benzenesulfonyl]-3-methyl-1H-indole dihydrochloride. | I.R (cm$^{-1}$): 3441, 2952, 1626, 1445, 1178, 914; $^1$H-NMR (ppm): 2.01-2.03 (5H, bs), 2.80 (3H, s), 3.11-3.13 (2H, m), 3.35-3.40 (2H, bs), 52 (4H, bs), 4.35 (2H, s), 7.15-7.19 (1H, m), 7.23-7.25 (2H, d, J = 7.71 Hz), 7.38-7.40 (1H, d, J = 7.71 Hz), 7.47-7.49 (1H, d, J = 8.58 Hz), 7.78 (1H, dd, J = 8.66, 2.03 Hz), 7.81-7.83 (1H, d, J = 8.22 Hz), 7.90 (1H, d, J = 1.99 Hz); Mass (m/z): 432.3 (M + H)$^+$. |

Examples 47-51

The person skilled in the art can prepare the compounds of Examples 47-51 by following the procedures described above.

| | |
|---|---|
| 47. | 2-Bromo-1-[3-(4-methyl piperazin-1-yl methyl) benzenesulfonyl]-1H-indole; |
| 48. | 4-Bromo-1-[3-(4-ethyl piperazin-1-yl methyl) benzenesulfonyl]-2-methyl-1H-indole; |
| 49. | 7-Chloro-1-[3-(4-methyl piperazin-1-yl methyl) benzenesulfonyl]-2-methyl-1H-indole; |
| 50. | 1-[2-Chloro-5-(4-methyl piperazin-1-yl methyl) benzenesulfonyl]-3-methyl-1H-indole; |
| 51. | 1-[2-Bromo-5-(4-methyl-[1,4]-diazepan-1-yl methyl) benzenesulfonyl]-5-chloro-3-methyl-1H-indole; |

Example 52

Tablet Comprising a Compound of Formula (I)

| | |
|---|---|
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients were combined and granulated using a solvent such as methanol. The formulation was then dried and formed into tablets (containing about 20 mg of active compound) with an appropriate tablet machine.

Example 53

Composition for Oral Administration

| Ingredient | % wt./wt. |
|---|---|
| Active ingredient | 20.0% |
| Lactose | 79.5% |
| Magnesium stearate | 0.5% |

The ingredients were mixed and dispensed into capsules containing about 100 mg each; one capsule would approximate a total daily dosage.

Example 54

Liquid Oral Formulation

| Ingredient | Amount |
|---|---|
| Active ingredient | 1.0 gram |
| Fumaric acid | 0.5 gram |
| Sodium chloride | 2.0 grams |
| Methyl paraben | 0.15 grams |
| Propyl paraben | 0.05 grams |
| Granulated sugar | 25.5 grams |
| Sorbitol (70% solution) | 12.85 grams |
| Veegum K (Vanderbilt Co.) | 1.0 gram |
| Flavoring | 0.035 gram |
| Coloring | 0.5 gram |
| Distilled water | q.s. to 100 mL |

The ingredients were mixed to form a suspension for oral administration.

Example 55

Parenteral Formulation

| Ingredient | % wt./wt. |
| --- | --- |
| Active ingredient | 0.25 gram |
| Sodium Chloride | qs to make isotonic |
| Water for injection | 100 mL |

The active ingredient was dissolved in a portion of the water for injection. A sufficient quantity of sodium chloride was then added with stirring to make the solution isotonic. The solution was made up to weight with the remainder of the water for injection, filtered through a 0.2 micron membrane filter and packaged under sterile conditions.

Example 56

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients were melted together and mixed on a steam bath and poured into molds containing 2.5 grams total weight.

Example 57

Topical Formulation

| Ingredients | Grams |
| --- | --- |
| Active ingredient | 0.2-2 grams |
| Span 60 | 2 grams |
| Tween 60 | 2 grams |
| Mineral oil | 5 grams |
| Petrolatum | 10 grams |
| Methyl paraben | 0.15 gram |
| Propyl paraben | 0.05 gram |
| BHA (butylated hydroxy anisole) | 0.01 gram |
| Water | 100 mL |

All of the ingredients, except, water, were combined and heated to about 60° C. with stirring. A sufficient quantity of water at about 60° C. was then added with vigorous stirring to emulsify the ingredients and then water added q.s about 100 grams.

Example 58

Binding Assay for Human 5-HT$_6$ Receptor

Compounds can be tested according to the following the procedures. Materials and Methods:
Receptor source: Human recombinant expressed in HEK293 cells
Radioligand: [$^3$H] LSD (60-80 Ci/mmol)
Final ligand concentration—[1.5 nM]
Non-specific determinant: Methiothepin mesylate—[0.1 µM]
Reference compound: Methiothepin mesylate
Positive control: Methiothepin mesylate
Incubation Conditions:
Reactions were carried out in 50 µM TRIS-HCl (pH 7.4) containing 10 µM MgCl$_2$, 0.5 mM EDTA for 60 minutes at 37° C. The reaction was terminated by rapid vacuum filtration onto glass fiber filters. Radioactivity trapped onto the filters was determined and compared to control values in order to ascertain any interactions of test compound(s) with the cloned serotonin 5-HT$_6$ binding site.

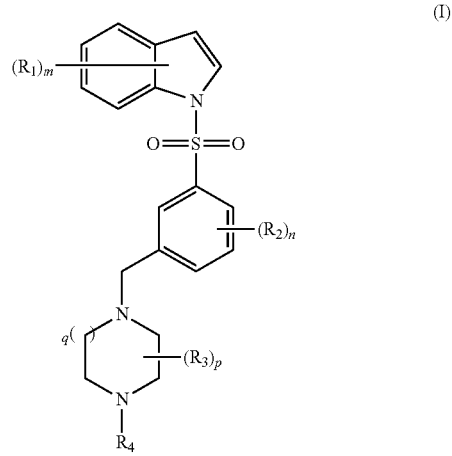

(I)

Percent Inhibition of Specific Binding at 100 nM Concentrations:

| Example Number | R$_1$ | R$_2$ | R$_3$ | R$_4$ | q | % Inhibition of specific binding at 100 nM |
| --- | --- | --- | --- | --- | --- | --- |
| 1. | H | 4'-Br | H | C$_2$H$_5$ | 1 | 78.91 |
| 3. | 5-OCH$_3$ | 4'-Br | H | C$_2$H$_5$ | 1 | 50.53 |
| 4. | 5-F | 4'-Br | H | C$_2$H$_5$ | 1 | 62.52 |
| 9. | 5-OCH$_3$ | H | H | CH$_3$ | 1 | 67.58 |
| 10. | 5-F | H | H | CH$_3$ | 1 | 79.20 |
| 11. | 5-OC$_2$H$_5$ | H | H | CH$_3$ | 1 | 63.73 |
| 13. | H | 4'-Cl | H | CH$_3$ | 1 | 83.29 |
| 14. | 5-F | 4'-Cl | H | CH$_3$ | 1 | 72.97 |
| 16. | 5-OCH$_3$ | 4'-Cl | H | CH$_3$ | 1 | 42.03 |
| 18. | 5-OCH$_3$ | 4'-Cl | H | C$_2$H$_5$ | 1 | 55.68 |
| 19. | 4-Cl | 4'-Cl | H | C$_2$H$_5$ | 1 | 81.99 |
| 20. | 4-Cl | 4'-Cl | H | CH$_3$ | 1 | 85.15 |
| 21. | H | 4'-Br | H | CH$_3$ | 1 | 88.79 |
| 24. | 5-OCH$_3$ | 4'-CH$_3$ | H | CH$_3$ | 1 | 62.18 |
| 25. | 5-F | 4'-Cl | H | C$_2$H$_5$ | 1 | 64.82 |
| 29. | 5-Br | 4'-Cl | H | C$_2$H$_5$ | 1 | 71.75 |
| 30. | 5-OCH$_3$, 3-CH$_3$ | 4'-Cl | H | C$_2$H$_5$ | 1 | 68.00 |
| 37. | 5-Br | 4'-Br | H | C$_2$H$_5$ | 1 | 55.86 |
| 39. | 3-CH$_3$ | 4'-Br | H | C$_2$H$_5$ | 1 | 91.51 |
| 43. | 5-F | 4'-CH$_3$ | H | CH$_3$ | 1 | 86.18 |
| 44. | 5-F | 4'-CH$_3$ | H | C$_2$H$_5$ | 1 | 78.54 |
| 45. | 3-CH$_3$ | 4'-Cl | H | C$_2$H$_5$ | 2 | 98.54 |
| 46. | 3-CH$_3$ | 4'-Cl | H | CH$_3$ | 2 | 92.24 |

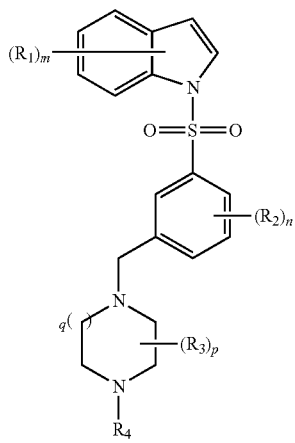

| Example Number | $R_1$ | $R_2$ | $R_3$ | $R_4$ | q | Ki (nM) |
|---|---|---|---|---|---|---|
| 8. | H | H | H | $CH_3$ | 1 | 1.91 |
| 15. | H | 4'-Cl | H | $C_2H_5$ | 1 | 18.4 |
| 22. | H | 4'-$CH_3$ | H | $CH_3$ | 1 | 7.01 |
| 23. | H | 4'-$CH_3$ | H | $C_2H_5$ | 1 | 3.96 |
| 35. | 3-$CH_3$ | 4'-Cl | H | $CH_3$ | 1 | 5.45 |
| 38. | 3-$CH_3$ | 4'-Br | H | $CH_3$ | 1 | 9.11 |

Literature Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

Example 59

5-$HT_6$ Functional Assay Cyclic AMP

The antagonist property of the compounds at the human 5-$HT_6$ receptors was determined by testing their effect on cAMP accumulation in stably transfected HEK293 cells. Binding of an agonist to the human 5-$HT_6$ receptor will lead to an increase in adenyl cyclase activity. A compound that is an, agonist will show an increase in cAMP production and a compound that is an antagonist will block the agonist effect.

Human 5-$HT_6$ receptors were cloned and stably expressed in HEK293 cells. These cells were plated in 6 well plates in DMEM/F12 media with 10% fetal calf serum (FCS) and 500 µg/mL G418 and incubated at 37° C. in a $CO_2$ incubator. The cells were allowed to grow to about 70% confluence before initiation of the experiment. On the day of the experiment, the culture media was removed and the cells were washed once with serum free medium (SFM). Two mL of SFM+IBMX media was added and incubated at 37° C. for 10 minutes. The media were removed and fresh SFM+IBMX media containing various compounds and 1 serotonin (as antagonist) were added to the appropriate wells and incubated for 30 minutes. Following incubation, the media were removed and the cells were washed once with 1 mL of PBS (phosphate buffered saline). Each well was treated with 1 mL cold 95% ethanol and 5 µM EDTA (2:1) at 4° C. for 1 hour. The cells were then scraped and transferred into Eppendorf tubes. The tubes, were centrifuged for 5 minutes at 4° C. and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 µl, peroxidase-labeled cAMP to the sample (100 µL) pre-incubated with the antiserum (100 mL) for 2 hours at 4° C. Following 1 hour incubation at 4° C., the unbound ligand is separated by a simple washing procedure. Then an enzyme substrate, trimethylbenzidine (1), is added and incubated at room temperature for 60 minutes. The reaction is stopped by the addition of 100 mL 1.0 M sulphuric acid and the resultant color read by a microtitre plate spectrophotometer at 450 nm within 30 minutes.

In the functional adenylyl cyclase assay, some of the compound of this invention was found to be a competitive antagonist with good selectivity over a number of other receptors including other serotonin receptors such as 5-$HT_{1A}$ and 5-$HT_7$.

Example 60

Rodent Pharmacokinetic Study

Male wistar rats (230-280 grams) obtained from NIN (National Institute of Nutrition, Hyderabad, India) were used as an experimental animal.

Three to five animals were housed in each cage. Animals were kept fasted over night and maintained on a 12 hours light/dark cycle. Three rats were dosed NCE (10 mg/Kg) orally and intravenously on day 0 and day 2.

At each time point blood was collected by jugular vein. Plasma was stored frozen at −20° C. until analysis. The concentrations of the NCE compound in plasma were determined using LC-MS/MS method.

Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/mL in plasma. Study samples were analyzed using calibration samples in the batch and quality control samples spread across the batch.

Pharmacokinetic parameters Cmax, Tmax, AUCt, AUCinf, half life, volume of distribution, clearance, mean residence time and thereby oral bioavailability were calculated by non-compartmental model using software WinNonlin version 5.1.

| Example Number | Strain/Sex | Dose (mg/kg) | Vehicle | Route of administration | Cmax (ng/mL) | Tmax (h) | $AUC_1$ (ng · hr/mL) | $T_{1/2}$ (h) | Bioavailab (%) |
|---|---|---|---|---|---|---|---|---|---|
| 22. | Wistar/Male | 10 | Water | Oral | 1375 ± 427 | 0.38 ± 0.18 | 3194 ± 1748 | 7.85 ± 2.62 | 30 ± 7 |
|  | Wistar/Male | 10 | Water | Intravenous | 4323 ± 1683 | 0.08 ± 0 | 5128 ± 1752 | 2.69 ± 1.51 |  |

-continued

| Example Number | Strain/Sex | Dose (mg/kg) | Vehicle | Route of administration | Cmax (ng/mL) | Tmax (h) | AUC$_1$ (ng·hr/mL) | T$_{1/2}$ (h) | Bioavailab (%) |
|---|---|---|---|---|---|---|---|---|---|
| 23. | Wistar/Male | 10 | Water | Oral | 749 ± 836 | 0.50 ± 0.43 | 1171 ± 1046 | 3.18 ± 1.71 | 14 ± 10 |
|  | Wistar/Male | 10 | Water | Intravenous | 4682 ± 617 | 0.08 ± 0 | 4073 ± 888 | 6.25 ± 0.35 |  |
| 35. | Wistar/Male | 10 | Water | Oral | 106 ± 1 | 0.38 ± 0.18 | 342 ± 152 | 1.73 ± 0.56 | 10 ± 6 |
|  | Wistar/Male | 10 | Water | Intravenous | 481 ± 331 | 0.08 ± 0 | 808 ± 156 | 5.84 ± 2.21 |  |

Example 61

Rodent Brain Penetration Study

Male Wister rats (230-280 grams) obtained from NIN (National Institute of Nutrition, Hyderabad, India) was used as an experimental animal. Three animals were housed in each cage. Animals were given water and food ad libitum throughout the experiment, and maintained on a 12 hours light/dark cycle.

Brain penetration was determined at steady state in rat. One day prior to dosing day, male wistar rats (225-250 grams) were anesthetized with halothane for surgical placement of jugular and femoral vein catheters. After surgery, the rats were housed in individual rat infusion cage connected with infusion components (Instech Solomon; Plymouth Meeting, Pa. USA) and allowed free access to food and water NCE compound was dissolved in water and administered at a constant infusion rate (5 ml/kg/hr) over 6-10 hours at a target dose rate of 1.0 mg free base/kg/h. Blood samples were removed during the latter part of the infusion to confirm steady-state blood concentrations, brain and blood was collected and estimated. Animals will be sacrificed to collect the plasma and brain tissue and was homogenized. Plasma and Brain was stored frozen at −20° C. until analysis. The concentrations of the NCE compound in plasma and Brain were determined using LC-MS/MS method.

The NCE compounds were quantified in plasma and brain homogenate by validated LC-MS/MS method using solid phase extraction technique. NCE compounds were quantified in the calibration range of 1-500 ng/mL in plasma and brain homogenate. Study samples were analyzed using calibration samples in the batch and quality control samples spread across the batch. atents of brain-blood ratio were calculated $(C_b/C_p)$.

| Example Number | Strain/Sex | Dose (mg/kg) | Vehicle | Route of administration | Steady State Brain Penetration $(C_b/C_p)$ |
|---|---|---|---|---|---|
| 22. | Wistar/Male | 10 | Water | Oral | 2.03 ± 0.42 |
| 23. | Wistar/Male | 10 | Water | Oral | 0.53 ± 0.13 |
| 35. | Wistar/Male | 10 | Water | Oral | 1.61 ± 0.39 |

Example 62

Rodent Brain Micro Dialysis Study for Possible Modulation of Neurotransmitters Male Wister rats (230-280 grams) obtained from N. I. N. (National Institute of Nutrition, Hyderabad, India) was used as experimental animals.

Group allocation Group 1: Vehicle (Water; 5 mL/kg; p.o.), Group 2: NCE (3 mg/kg; p.o.), Group 3: NCE (10 mg/kg; p.o.)

Surgical Procedure: Rats were anesthetized with chloral hydrate and placed in Stereotaxic frame. Guide cannula (CMA/12) was placed at AP: −5.2 mm, ML: +5.0 mm relative from bregma and DV: −3.8 mm from the brain surface according to the atlas of Paxinos and Watson (1986). While the animal was still anesthetized, a micro dialysis probe (CMA/12, 4 mm, PC) was inserted through the guide cannula and secured in place. After surgery recovery period of 48-72 hours was maintained before subjecting the animal for study.

A day prior to study animals were transferred to home cages for acclimatization and implanted probe was perfused overnight with a modified Ringer's solution comprised of: 1.3 µM CaCl2 (Sigma), 1.0 µM MgCl$_2$ (Sigma), 3.0 µM KCl (Sigma), 147.0 µM NaCl (Sigma), 1.0 µM Na$_2$HPO$_4$.7H$_2$O and 0.2 µM NaH$_2$PO$_4$.2 H$_2$O and and 0.3 µM neostigmine bromide (Sigma) (pH to 7.2) at a rate of 0.2 µL/minute set by a microinfusion pump (PicoPlus, Harward). On the day of experiment perfusion rate was changed to 1.2 µL/minutes and allowed for 3 hours stabilization. After stabilization period, four basals were collected at 20 minutes intervals before dosing. Dialysate samples were collected in glass vials using CMA/170 refrigerated fraction collector.

Vehicle or NCE (3 mg/kg or 10 mg/kg) was administered by gavage after four fractions had been collected. The perfusate was collected until 6 hours, after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50µ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 µL) of the four samples before drug administration:

Effects of NCE (3 & 10 mg/kg) and Vehicle treatments were statistically evaluated by one-way ANOVA followed by Dunnett's multiple comparison tests. In all statistical measures, a p <0.05 was considered significant. The Graph Pad Prism program statistically evaluated the data.

Example 63

Food Intake Measurement

Male Wister rats (120-140 grams) obtained from N. I. N. (National Institute of Nutrition, Hyderabad, India) was used.

The chronic effect of the compounds of general formula (I) on food intake in well-fed rats was then determined as follows.

The rats were housed in single home cages for 28 days. During this period, the rats were either dosed orally or ip, with a composition comprising a compound of formula (I) or a corresponding composition (vehicle) without the said compound (control group), once a day. The rat is provided with ad libitum food and water.

On 0, $1^{st}$, $7^{th}$, $14^{th}$, $21^{st}$ and $28^{th}$ day the rats were left with the pre-weighed amounts of food. Food intake and weight gain were measured on a routine basis. Also a food ingestion method is disclosed in the literature (Kask et al., European Journal of Pharmacology, 414, 2001, 215-224 and Turnball et. al., Diabetes, vol 51, August, 2002, and some in-house modifications.). The respective parts of the descriptions are herein incorporated as a reference and they form part of the disclosure.

Some representative compounds have shown the statistically significant decrease in food intake, when conducted in the above manner at the doses of either 10 mg/Kg or 30 mg/Kg or both

Example 64

Object Recognition Task Model

The cognition-enhancing properties of compounds of this invention were estimated using a model of animal cognition: the object recognition task model.

Male Wister rats (230-280 grams) obtained from N. I. N. (National Institute of Nutrition, Hyderabad, India) were used as experimental animals. Four animals were housed in each cage. Animals were kept on 20% food deprivation before one day and given water ad libitum throughout the experiment and-maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarilation phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were, placed in T1 trial. Choice phase (T2) rats were allowed to explore the open field for 3 minutes in presence of one familiar object (a3) and one novel object (b) (Amber color glass'bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed. T1 is the total time spent exploring the familiar objects (a1+a2). T2 is the total time spent exploring the familiar object and novel object (a3+b).

The object recognition test was performed as described by Ennaceur, A., Delacour, J., 1988, A new one-trial test for neurobiological studies of memory in rats—Behavioral data, Behav. Brain Res., 31, 47-59.

Some representative compounds have shown positive effects indicating the increased novel object recognition viz; increased exploration time with novel object and higher discrimination index.

| Example Number | NORT Discriminative Index (DI) = Treatment (Vehicle) | | Inference |
|---|---|---|---|
| | 10 mg/kg, p.o. | 30 mg/kg, p.o. | |
| 8. | 0.58 (0.45) | — | Active |
| 22. | 0.57 (0.54) | — | Active |
| 23. | — | 0.58 (0.49) | Active |
| 35. | — | 0.63 (0.49) | Active |

Example 65

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm² perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape, learning. An automated tracking system, [Videomot 2 (5.51), TSE systems, Germany] was employed. This program analyzes video images acquired via a digital camera and an image acquisition board that determined path length, swim speed and the number of dutation of swim time spent in each quadrant of the water maze.

| Example Number | Scopolamine Induced Reversal |
|---|---|
| 8. | ≧30 mg/kg, p.o |
| 22. | >30 mg/kg, p.o |
| 23. | ≧30 mg/kg, p.o |
| 35. | >30 mg/kg, p.o |

Example 66

Chewing/Yawning/Stretching Induction by $5\text{-}HT_6$ R Antagonists

Male Wister rats weighing 200-250 grams were used. Rats were given vehicle injections and placed in individual, transparent chambers for 1 hour each day for 2 days before the test day, to habituate them to the observation chambers and testing procedure. On the test day, rats were placed in the observation chambers immediately after drug administration and observed continuously for yawning, stretching, and chewing behaviors from 60 to 90 minutes after drug or vehicle injections. 60 minutes prior to the drug administration Physostigmine, 0.1 mg/kg i.p, was administered to all the animals. Average number of yawns, stretches and vacuous chewing movements during the 30 minutes observation period were recorded.

Reference: (A) King M. V., Sleight A., J., Woolley M. L., and et. al., Neuropharmacology, 2004, 47, 195-204. (B) Bentey J. C., Bourson A., Boess F. G., Fone K. C. F., Marsden C. A., Petit N., Sleight A. J., British Journal of Pharmacology, 1999, 126 (7), 1537-1542).

Example 67

Passive Avoidance

Animals were trained in a single-trial, step through, light-dark passive avoidance paradigm. The training apparatus consisted of a chamber 300 mm in length, 260 mm wide, and 270 mm in height, constructed to established designs. The front and top were transparent, allowing the experimenter to observe the behavior of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 seconds across the 16 bars. A resistance range of 40-60 micro ohms was calculated for a control group of rats and the apparatus was calibrated accordingly. An electronic circuit detecting the resistance of the animal ensured an accurate current delivery by automatic variation of the voltage with change in resistance.

Experimental Procedure

This was carried out as described previously. Adult male Wister rats weighing 200-230 grams were used. Animals were brought to the laboratory 1 hour before the experiment. On the day of training, animals were placed facing the rear of the light compartment of the apparatus. The timer was started once the animal has completely turned to face the front of the chamber. Latency to enter the dark chamber was recorded (usually <20 seconds) and having completely entered the dark compartment an inescapable foot shock of 0.75 mA for 3 seconds was administered to the animal. Animals were then returned to their home cages. Between each training session, both compartments of the chamber were cleaned to remove any confounding olfactory cues. Recall of this inhibitory stimulus was evaluated 24 hours, 72 hours and on 7 day post-training by returning the animal into the light chamber and recording their latency to enter the dark chamber, a criterion time of 300 seconds was employed.

Reference: (A) Callahan P. M., Rowe N. B., Tehim A., Abst. 776.19.2004; Society for neuroscience, 2004. (B) Fox G. B., Connell A. W. U., Murphy K. J., Regan C. M., Journal of Neurochemistry, 1995, 65, 6, 2796-2799.

We claim:
1. A compound of the formula (I),

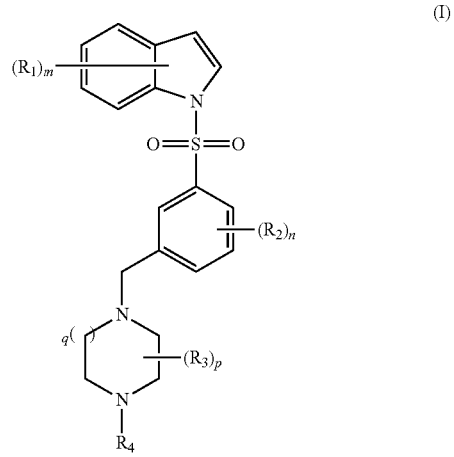

wherein,
$R_1$ and $R_2$ may be the same or different and each independently selected from hydrogen, halogen, $(C_1-C_3)$alkyl or $(C_1-C_3)$alkoxy;
$R_3$ is hydrogen;
$R_4$ is hydrogen or $(C_1-C_3)$alkyl;
"m" is an integer ranging from 0 to 6;
"n" is an integer ranging from 0 to 4;
"p" is an integer ranging from 0 to 5;
"q" is an integer ranging from 0 to 2;
or its pharmaceutically acceptable salts.

2. The compound according to claim 1, which is selected from the group consisting of:
1- [4-Bromo-3-(4-ethyl piperazin-1-yl methyl) benzenesulfonyl]-1 H-indole;
1-[4-Bromo-3-(4-methyl piperazin-1-yl methyl) benzenesulfonyl]-5-methoxy-1H-indole;
1-[4-Bromo-3-(4-ethyl piperazin-1-yl methyl) benzenesulfonyl]-5-methoxy-1H-indole;
1-[4-Bromo-3-(4-ethyl piperazin-1-yl methyl) benzenesulfonyl]-5-fluoro-1H-indole;
1-[4-Chloro-3-(4-methyl piperazin-1-yl methyl) benzenesulfonyl]-5-fluoro-3-bromo-1H-indole;
5-Isopropoxy-1-[3-(4-methyl piperazin-1-yl methyl) benzenesulfonyl]-1H-indole;
4-Chloro-1-[3-(4-methyl piperazin-1-yl methyl) benzenesulfonyl]-1H-indole;
1-[3-(4-Methyl piperazin-1-yl methyl) benzenesulfonyl] 1H -indole;
5-Methoxy-1-[3-(4-methyl piperazin-1-yl methyl) benzenesulfonyl]-1H-indole;
5-Fluoro-1-[3-(4-methyl piperazin-1-yl methyl) benzenesulfonyl]-1H-indole;
5-Ethoxy-1-[3-(4-methyl piperazin-1-yl methyl) benzenesulfonyl]-1H-indole;
1-[4-Bromo-3-(4-ethyl piperazin-1-yl methyl) benzenesulfonyl]-1H-indole dihydrochloride;
1-[4-Chloro-3-(4-methyl piperazin-1-yl methyl) benzenesulfonyl]-1H-indole dihydrochloride;
1-[4-Chloro-3-(4-methyl piperazin-1-yl methyl) benzenesulfonyl]-5-fluoro-1H-indole dihydrochloride;
1-[4-Chloro-3-(4-ethyl piperazin-1-yl methyl) benzenesulfonyl]-1H-Indole dihydrochloride;

1-[4-Chloro-3-(4-methyl piperazin-1-yl methyl) benzenesulfonyl]-5-methoxy-1H-indole dihydrochloride;
1-[4-Chloro-3-(4-methyl piperazin-1-yl methyl) benzenesulfonyl]-5-bromo-1H-indole dihydrochloride;
1-[4-Chloro-3-(4-ethyl piperazin-1-yl methyl) benzenesulfonyl]-5-methoxy-1H-indole dihydrochloride;
1-[4-Chloro-3-(4-ethyl piperazin-1-yl methyl) benzenesulfonyl]-4-chloro-1H-indole dihydrochloride;
1-[4-Chloro-3-(4-methyl piperazin-1-yl methyl) benzenesulfonyl]-4-chloro-1H-indole dihydrochloride;
1-[4-Bromo-3-(4-methyl piperazin-1-yl methyl) benzenesulfonyl]-1H-indole dihydrochloride;
1-[4-methyl-3-(4-methyl piperazin-1-yl methyl) benzenesulfonyl]-1H-indole dihydrochloride;
1-[4-methyl-3-(4-ethyl piperazin-1-yl methyl) benzenesulfonyl]-1H-indole dihydrochloride;
1-[4-methyl-3-(4-methyl piperazin-1-yl methyl) benzenesulfonyl]-5-methoxy-1H-indole dihydrochloride;
1-[4-Chloro-3-(4-ethyl piperazin-1-yl methyl) benzenesulfonyl]-5-fluoro-1H-indole dihydrochloride;
1-[4-Bromo-3-(4-methyl piperazin-1-yl methyl) benzenesulfonyl]-5-fluoro-1H-indole dihydrochloride;
1-[4-Bromo-3-(4-methyl piperazin-1-yl methyl) benzenesulfonyl]-5-methoxy-3-methyl-1H-indole dihydrochloride;
1-[4-Bromo-3-(4-ethyl piperazin-1-yl methyl) benzenesulfonyl]-5-methoxy-3-methyl-1H-indole dihydrochloride;
1-[4-Chloro-3-(4-ethyl piperazin-1-yl methyl) benzenesulfonyl]-5-bromo-1H-indole dihydrochloride;
1-[4-Chloro-3-(4-ethyl piperazin-1-yl methyl) benzenesulfonyl]-5-methoxy-3-methyl-1H-indole dihydrochloride;
1-[4-Chloro-3-(4-methyl piperazin-1-yl methyl) benzenesulfonyl]-5-methoxy-3-methyl-1H-indole dihydrochloride;
1-[4-Chloro-3-(4-methyl piperazin-1-yl methyl) benzenesulfonyl]-5-methoxy-3-bromo-1H-indole dihydrochloride;
1-[4-Chloro-3-(4-ethyl piperazin-1-yl methyl) benzenesulfonyl]-5-methoxy-3-bromo-1H-indole dihydrochloride;
1-[4-Chloro-3-(4-ethyl piperazin-1-yl methyl) benzenesulfonyl]-3-methyl-1H-indole dihydrochloride;
1-[4-Chloro-3-(4-methyl piperazin-1-yl methyl) benzenesulfonyl]-3-methyl-1H-indole dihydrochloride;
1-[4-Bromo-3-(4-methyl piperazin-1-yl methyl) benzenesulfonyl]-5-bromo-1H-indole dihydrochloride;
1-[4-Bromo-3-(4-ethyl piperazin-1-yl methyl) benzenesulfonyl]-5-bromo-1H-indole dihydrochloride;
1-[4-Bromo-3-(4-methyl piperazin-1-yl methyl) benzenesulfonyl]-3-methyl-1H-indole dihydrochloride;
1-[4-Bromo-3-(4-ethyl piperazin-1-yl methyl) benzenesulfonyl]-3-methyl-1H-indole dihydrochloride;
1-[4-Methyl-3-(4-ethyl piperazin-1-yl methyl) benzenesulfonyl]-5-methoxy-3-methyl-1H-indole dihydrochloride;
1-[4-Methyl-3-(4-methyl piperazin-1-yl methyl) benzenesulfonyl]-5-methoxy-3-methyl-1H-indole dihydrochloride;
1-[4-Methyl-3-(4-ethyl piperazin-1-yl methyl) benzenesulfonyl]-5-methoxy-1H-indole dihydrochloride;
1-[4-Methyl-3-(4-methyl piperazin-1-yl methyl) benzenesulfonyl]-5-fluoro-1H-indole dihydrochloride;
1-[4-Methyl-3-(4-ethyl piperazin-1-yl methyl) benzenesulfonyl]-5-fluoro-1H-indole dihydrochloride;
1-[4-Chloro-3-(4-ethyl-[1,4]diazepan-1-yl methyl) benzenesulfonyl]-3-methyl-1H-indole dihydrochloride;
1-[4-Chloro-3-(4-methyl[1,4]diazepan-1-yl methyl) benzenesulfonyl]-3-methyl-1H-indole dihydrochloride;
2-Bromo-1-[3-(4-methyl piperazin-1-yl methyl) benzenesulfonyl]-1H-indole;
4-Bromo-1-[3-(4-ethyl piperazin-1-yl methyl) benzenesulfonyl]-2-methyl-1H-indole;
7-Chloro-1-[3-(4-methyl piperazin-1-yl methyl) benzenesulfonyl]-2-methyl-1H-indole;
1-[2-Chloro-5-(4-methyl piperazin-1-yl methyl) benzenesulfonyl]-3-methyl-1H-indole and 1-[2-Bromo-5-(4-methyl-[1,4]-diazepan-1-yl methyl) benzenesulfonyl]-5-chloro-3-methyl-1H-indole; or its pharmaceutically acceptable salts.

3. A process for preparation of compound of formula (I)

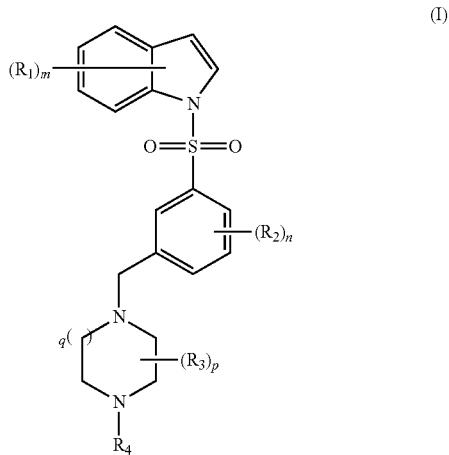

(I)

comprising:
Contacting a compound of formula (III),

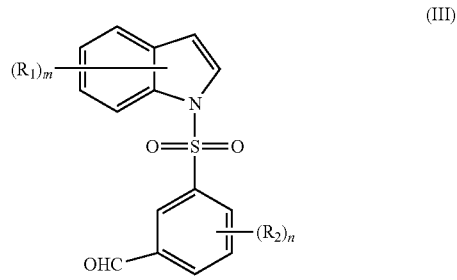

(III)

with compound of formula (IV) by reductive amination,

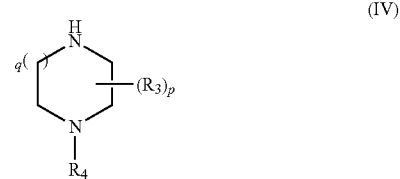

(IV)

by using a suitable reducing agent in presence of inert solvent at suitable temperature to obtain a compound of formula (I), wherein:

$R_1$ and $R_2$ may be the same or different and each independently selected from hydrogen, halogen, $(C_1\text{-}C_3)$alkyl or $(C_1\text{-}C_3)$alkoxy;
$R_3$ is hydrogen;
$R_4$ is hydrogen or $(C_1\text{-}C_3)$alkyl;
"m" is an integer ranging from 0 to 6;
"n" is an integer ranging from 0 to 4;
"p" is an integer ranging from 0 to 5;
"q" is an integer ranging from 0 to 2.

4. A pharmaceutical composition comprising a compound according to formula (I)

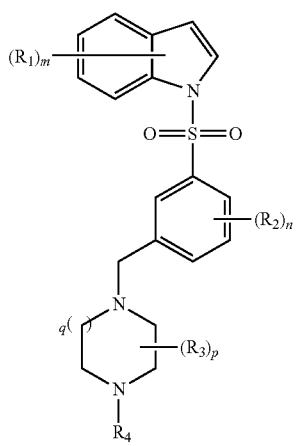

wherein,
$R_1$ and $R_2$ may be the same or different and each independently selected from hydrogen, halogen, $(C_1\text{-}C_3)$alkyl or $(C_1\text{-}C_3)$alkoxy;
$R_3$ is hydrogen;
$R_4$ is hydrogen or $(C_1\text{-}C_3)$alkyl;
"m" is an integer ranging from 0 to 6;
"n" is an integer ranging from 0 to 4;
"p" is an integer ranging from 0 to 5;
"q" is an integer ranging from 0 to 2; or its pharmaceutically acceptable salts;
and pharmaceutically acceptable excipients.

5. A method for enhancing cognition and memory in a patient in need thereof, which comprise providing to said patient a compound of formula (I):

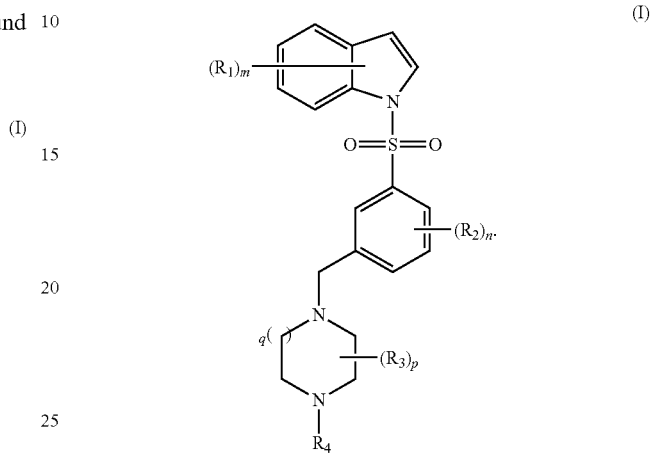

wherein,
$R_1$ and $R_2$ may be the same or different and each independently selected from hydrogen, halogen, $(C_1\text{-}C_3)$alkyl or $(C_1\text{-}C_3)$alkoxy;
$R_3$ is hydrogen;
$R_4$ is hydrogen or $(C_1\text{-}C_3)$alkyl;
"M" is an integer ranging from 0 to 6;
"n" is an integer ranging from 0 to 4;
"p" is an integer ranging from 0 to 5;
"q" is an integer ranging from 0 to 2;
or its pharmaceutically acceptable salts.

* * * * *